(12) United States Patent
Pitre et al.

(10) Patent No.: US 10,474,875 B2
(45) Date of Patent: Nov. 12, 2019

(54) IMAGE ANALYSIS USING A SEMICONDUCTOR PROCESSOR FOR FACIAL EVALUATION

(71) Applicant: Affectiva, Inc., Waltham, MA (US)

(72) Inventors: Boisy G Pitre, Opelousas, LA (US); Rana el Kaliouby, Milton, MA (US); Panu James Turcot, San Francisco, CA (US)

(73) Assignee: Affectiva, Inc., Boston, MA (US)

( * ) Notice: Subject to any disclaimer, the term of this patent is extended or adjusted under 35 U.S.C. 154(b) by 789 days.

(21) Appl. No.: 14/947,789

(22) Filed: Nov. 20, 2015

(65) Prior Publication Data

US 2016/0078279 A1    Mar. 17, 2016

Related U.S. Application Data

(63) Continuation-in-part of application No. 13/153,745, filed on Jun. 6, 2011, now abandoned, and a
(Continued)

(51) Int. Cl.
*G06K 9/00* (2006.01)
*A61B 5/16* (2006.01)
(Continued)

(52) U.S. Cl.
CPC .......... *G06K 9/00228* (2013.01); *A61B 5/165* (2013.01); *A61B 5/7264* (2013.01);
(Continued)

(58) Field of Classification Search
CPC .......... G06K 9/00275; G06K 9/00281; G06K 9/0028; G06K 9/00295; G06K 9/00302;
(Continued)

(56) References Cited

U.S. PATENT DOCUMENTS 3,034,500 A    5/1962  Backster, Jr.
3,548,806 A   12/1970  Fisher
(Continued)

FOREIGN PATENT DOCUMENTS

JP            08115367       7/1996
KR   10-2005-0021759 A      3/2005
(Continued)

OTHER PUBLICATIONS

Albiol, Alberto, et al. "Face recognition using HOG-EBGM." Pattern Recognition Letters 29.10 (2008): 1537-1543.
(Continued)

*Primary Examiner* — Wesley J Tucker
(74) *Attorney, Agent, or Firm* — Adams Intellex, PLC

(57) ABSTRACT

Image analysis for facial evaluation is performed using logic encoded in a semiconductor processor. The semiconductor chip analyzes video images that are captured using one or more cameras and evaluates the videos to identify one or more persons in the videos. When a person is identified, the semiconductor chip locates the face of the evaluated person in the video. Facial regions of interest are extracted and differences in the regions of interest in the face are identified. The semiconductor chip uses classifiers to map facial regions for emotional response content and evaluate the emotional response content to produce an emotion score. The classifiers provide gender, age, or ethnicity with an associated probability. Localization logic within the chip is used to localize a second face when one is evaluated in the video. The one or more faces are tracked, and identifiers for the faces are provided.

28 Claims, 14 Drawing Sheets

Related U.S. Application Data continuation-in-part of application No. 14/460,915, filed on Aug. 15, 2014, which is a continuation-in-part of application No. 13/153,745, filed on Jun. 6, 2011, now abandoned, application No. 14/947,789, which is a continuation-in-part of application No. 14/460,915, filed on Aug. 15, 2014, and a continuation-in-part of application No. 13/153,745, filed on Jun. 6, 2011, now abandoned, application No. 14/947,789, which is a continuation-in-part of application No. 13/708,027, filed on Dec. 7, 2012, now abandoned.

(60) Provisional application No. 62/082,579, filed on Nov. 20, 2014, provisional application No. 62/128,974, filed on Mar. 5, 2015, provisional application No. 62/217,872, filed on Sep. 12, 2015, provisional application No. 62/222,518, filed on Sep. 23, 2015, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/867,007, filed on Aug. 16, 2013, provisional application No. 61/924,252, filed on Jan. 7, 2014, provisional application No. 61/916,190, filed on Dec. 14, 2013, provisional application No. 61/927,481, filed on Jan. 15, 2014, provisional application No. 61/953,878, filed on Mar. 16, 2014, provisional application No. 61/972,314, filed on Mar. 30, 2014, provisional application No. 62/023,800, filed on Jul. 11, 2014, provisional application No. 61/568,130, filed on Dec. 7, 2011, provisional application No. 61/581,913, filed on Dec. 30, 2011.

(51) Int. Cl.
*A61B 5/00* (2006.01)
*G06T 7/11* (2017.01)
*G16H 50/70* (2018.01)
*G16H 30/40* (2018.01)
*G16H 50/30* (2018.01)
*G16H 20/70* (2018.01)

(52) U.S. Cl.
CPC ............ *G06K 9/00281* (2013.01); *G06T 7/11* (2017.01); *G16H 20/70* (2018.01); *G16H 30/40* (2018.01); *G16H 50/30* (2018.01); *G16H 50/70* (2018.01); *A61B 5/0077* (2013.01); *A61B 5/6898* (2013.01)

(58) Field of Classification Search
CPC ........... G06K 9/00308; G06K 9/00315; G06K 9/00335; G06K 9/00342; G06K 9/00348; G06K 9/00355; G06K 9/00362; G06K 9/00241
See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | MacLean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,121,953 A * | 9/2000 | Walker .................... G06F 3/011 2/421 |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |

(56) References Cited

U.S. PATENT DOCUMENTS

| | | |
|---|---|---|
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,747,801 B2 | 6/2010 | Han et al. |
| 7,757,171 B1 | 7/2010 | Wong et al. |
| 7,757,231 B2 | 7/2010 | Anderson et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,170,609 B2 | 5/2012 | Hedtke et al. |
| 8,219,438 B1 | 7/2012 | Moon et al. |
| 8,374,240 B1 | 2/2013 | Namboodiri et al. |
| 8,401,248 B1 | 3/2013 | Moon et al. |
| 8,402,543 B1 | 3/2013 | Ranjan et al. |
| 8,442,638 B2 | 5/2013 | Libbus et al. |
| 8,522,779 B2 | 9/2013 | Lee et al. |
| 8,560,972 B2 | 10/2013 | Wilson |
| 8,600,120 B2 | 12/2013 | Gonion et al. |
| 8,640,021 B2 | 1/2014 | Perez et al. |
| 8,649,612 B1 | 2/2014 | Brunner |
| 8,725,662 B2 | 5/2014 | Izhikevich et al. |
| 8,755,837 B2 | 6/2014 | Rhoads et al. |
| 8,832,688 B2 | 9/2014 | Tang et al. |
| 9,579,057 B2* | 2/2017 | Bradu ............... A61B 5/4839 |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0115157 A1* | 6/2006 | Mori ............... G06K 9/00221 382/190 |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0170123 A1* | 7/2008 | Albertson ......... A63B 24/0003 348/157 |
| 2008/0184170 A1 | 7/2008 | Periyalwar |
| 2008/0185207 A1* | 8/2008 | Kondoh ............... B60W 30/16 180/272 |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2008/0318624 A1 | 12/2008 | Hedtke et al. |
| 2009/0002178 A1 | 1/2009 | Guday et al. |
| 2009/0006206 A1 | 1/2009 | Groe |
| 2009/0080763 A1 | 3/2009 | Jau et al. |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0164132 A1 | 6/2009 | Jung et al. |
| 2009/0210290 A1 | 8/2009 | Elliott et al. |
| 2009/0217315 A1* | 8/2009 | Malik ............... G06K 9/00362 725/9 |
| 2009/0259518 A1 | 10/2009 | Harvey |
| 2009/0270170 A1 | 10/2009 | Patton |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0102643 A1 | 5/2011 | Nanu et al. |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0114172 A1 | 5/2012 | Du et al. |
| 2012/0195368 A1 | 8/2012 | Chien et al. |
| 2012/0290508 A1* | 11/2012 | Bist ............... G06F 17/30035 706/10 |
| 2012/0324491 A1 | 12/2012 | Bathiche et al. |
| 2013/0023337 A1 | 1/2013 | Bowers et al. |
| 2013/0116587 A1 | 5/2013 | Sornmo et al. |
| 2013/0156304 A1 | 6/2013 | Moorty et al. |
| 2013/0197409 A1 | 8/2013 | Baxter et al. |
| 2013/0273968 A1 | 10/2013 | Rhoads et al. |
| 2013/0287114 A1 | 10/2013 | Arevalo Baeza et al. |
| 2013/0304363 A1 | 11/2013 | Dai et al. |
| 2013/0335318 A1 | 12/2013 | Nagel et al. |
| 2014/0100835 A1 | 4/2014 | Majumdar et al. |
| 2014/0154649 A1 | 6/2014 | Farley et al. |
| 2014/0172910 A1 | 6/2014 | Jung et al. |
| 2014/0253666 A1 | 9/2014 | Ramachandran et al. |
| 2014/0277718 A1 | 9/2014 | Izhikevich et al. |
| 2014/0278455 A1* | 9/2014 | Chandrasekaran ............... G06Q 30/0203 705/2 |
| 2016/0104486 A1 | 4/2016 | Penilla et al. |
| 2017/0003784 A1 | 1/2017 | Garg et al. |
| 2019/0138096 A1* | 5/2019 | Lee ............... G06F 3/015 |

FOREIGN PATENT DOCUMENTS

| | | |
|---|---|---|
| KR | 10-2008-0016303 A | 2/2008 |
| KR | 1020100048688 A | 5/2010 |
| WO | WO 2011/045422 A1 | 4/2011 |

OTHER PUBLICATIONS

Rana Ayman El Kaliouby, Mind-reading machines: automated inference of complex mental states, Jul. 2005, University of Cambridge, Cambridge, United Kingdom.

(56) References Cited

OTHER PUBLICATIONS

International Search Report dated Nov. 14, 2011 for PCT/US2011/39282.
International Search Report dated Apr. 16, 2012 for PCT/US2011/054125.
International Search Report dated May 24, 2012 for PCT/US2011/060900.
Xiaoyu Wang, An HOG-LBP human detector with partial occlusion handling, Sep. 29, 2009, IEEE 12th International Conference on Computer Vision, Kyoto, Japan.
Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.
Nicholas R. Howe and Amanda Ricketson, Improving the Boosted Correlogram, 2004, Lecture Notes in Computer Science, ISSN 0302-9743, Springer-Verlag, Germany.
Xuming He, et al, Learning and Incorporating Top-Down Cues in Image Segmentation, 2006, Lecture Notes in Computer Science, ISBN 978-3-540-33832-1, Springer-Verlag, Germany.
Ross Eaton, et al, Rapid Training of Image Classifiers through Adaptive, Multi-frame Sampling Methods, Oct. 2008, IEEE 37th Applied Imagery Pattern Recognition Workshop, Washington DC.
Verkruysse, Wim, Lars O. Svaasand, and J. Stuart Nelson. "Remote plethysmographic imaging using ambient light." Optics express 16.26 (2008): 21434-21445.

\* cited by examiner

IMAGE ANALYSIS USING A SEMICONDUCTOR PROCESSOR FOR FACIAL EVALUATION

RELATED APPLICATIONS

This application claims the benefit of U.S. provisional patent applications "Semiconductor Based Mental State Analysis" Ser. No. 62/082,579, filed Nov. 20, 2014, "Viewership Analysis Based on Facial Evaluation" Ser. No. 62/128,974, filed Mar. 5, 2015, "Mental State Event Signature Usage" Ser. No. 62/217,872, filed Sep. 12, 2015, and "Image Analysis In Support of Robotic Manipulation" Ser. No. 62/222,518, filed Sep. 23, 2015. This application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. This application is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014; the application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. This application is also a continuation-in-part of U.S. patent application "Mental State Evaluation Learning for Advertising" Ser. No. 13/708,027, Dec. 7, 2012, which claims the benefit of U.S. provisional patent applications "Mental State Evaluation Learning for Advertising" Ser. No. 61/568,130, filed Dec. 7, 2011 and "Affect Based Evaluation of Advertisement Effectiveness" Ser. No. 61/581,913, filed Dec. 30, 2011; the application is also a continuation-in-part of U.S. patent application "Mental State Analysis Using Web Services" Ser. No. 13/153,745, filed Jun. 6, 2011 which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of images and more particularly to image analysis using a semiconductor processor for facial evaluation.

BACKGROUND

On any given day, an individual experiences various external stimuli that can provoke a wide range of responses. The responses of the individual can manifest in mental and emotional states, facial expressions, body language, and so on. The stimuli are perceived through one or more senses and can be visual, aural, olfactory, tactile, and so on. Alone or in combination, the stimuli can invoke strong emotions and mental states in the individual who experiences them. Not all individuals experiencing the one or more stimuli will react in a similar manner. That is, when a group of individuals experiences the stimuli, the reactions can be at times similar, at other times widely varied, and so on. How an individual reacts to experienced stimuli can be important to defining the essence of an individual. Furthermore, the individual's responses to the stimuli can have a profound impact on the mental states experienced by the individual.

The mental states that an individual can have in response to external stimuli can vary depending on time frames; such as one time of day versus another, one day to another, and so on. An individual's mental state is important to general well-being and impacts her or his perception of the surrounding environment, decision-making processes, and so on. Multiple individuals' mental states that result from a common event can carry a collective importance, where the collective importance can be, in certain circumstances, even more significant than the importance of each individual's mental state. The mental states of an individual or a group of individuals can vary widely, ranging from happiness to sadness, from contentedness to worry, and from calm to excitement, to name only a few possible states. Despite how critical and influential one's mental states are to daily life, the mental state of a single individual, let alone those of a group, might not always be apparent, even to that individual. The ability and means by which one person perceives her or his emotional state can be quite difficult to summarize. Though an individual can often perceive her or his own emotional state quickly, instinctively, and with little or no conscious effort, the individual might encounter difficulty when attempting to summarize or communicate her or his mental state to others. This difficulty of understanding and communicating mental states becomes far more complex when the mental states of multiple individuals are considered.

Gaining an insight into the mental states of one or more individuals is an important technique for understanding how people react to various external stimuli such as views of the natural landscape, political and sports events, educational programs, natural disasters, etc. However, proper interpretation of mental states is very difficult when the individuals being considered are themselves unable to accurately identify and communicate their mental states. The identification and communication of mental states can be further complicated by the fact that multiple individuals can have similar or very different mental states when taking part in a communal activity. For example, the mental state of two friends viewing an important political debate can be disparate—if one friend is a supporter of the winning candidate, while the other friend is a supporter of the losing candidate, it is reasonable to expect widely varying mental states between the two friends. However, the problem of defining the resulting mental states from multiple people experiencing complex stimuli can be a considerably complicated exercise.

SUMMARY

Modern electronic devices are constructed with a variety of special-purpose hardware that is integral to the devices. This special-purpose hardware enables the devices to be used to support a variety of additional functions. For example, a typical smart phone includes not only the battery, radios, and keyboard required to support telephony, SMS (text), and other common features, but also cameras, displays, haptic input devices, accelerometers, global positioning systems (GPS), audio codecs, microphones, and so on. This special-purpose hardware vastly expands the capabilities and usefulness of the electronic devices by enabling the devices to support mapping, positioning, video communications, social networking, etc. As additional hardware is added to the electronic devices, new and emerging capabilities further expand the usefulness of the devices.

Social networking is an area that can take advantage of many of the special-purpose hardware features and capabilities. The cameras are used for video calls and chats, the GPS for finding friends, the display for sharing pictures and videos, and so on. Social networking can also give a sense of a viewer's disposition to a friend's online content by supporting "likes", comments, and so on. However, subtleties in the postings and in the responses can be lost. For example, one would never "like" the news that a friend's beloved pet is missing but rather might be very engaged and post a comment expressing sympathy, or a friend's sarcastic post about his "best date ever" could easily be misread or misinterpreted, resulting in embarrassing comments. These issues and many others can be overcome by including special-purpose hardware in the devices that can be used to evaluate the emotional responses of users of social and other media. Such hardware can support a variety of applications and enable various capabilities.

Logic devices can be used to analyze data including video data and physiological data that can be collected using cameras, sensors, accelerometers, and so on. When the collected data includes video data such as videos, video segments, still images, etc., then the video data in turn can be checked for the presence of images of one or more persons. The videos are evaluated for the bodies of the one or more persons, and a face associated with one of the bodies is localized. Facial regions of interest (ROI) are extracted from the localized face, and differences in the regions of interest within the face are identified. Classifiers are used to map facial regions for emotional response content. The emotional response content is evaluated to produce an emotion score, where the emotion score can be based on the face that was localized in the videos. The emotion response content of any number of other faces that are localized in the video can be evaluated and emotion scores generated based on each of the localized faces.

The emotional scores of one or more people are determined using semiconductor-based logic that is used for mental state analysis. An apparatus for analysis is described comprising: a device containing image analysis logic encoded in a semiconductor chip comprising: evaluation logic that evaluates bodies of one or more persons in videos; localization logic that performs localization of a face within the videos, where the face is from one of the bodies of the one or more persons; feature extraction logic that performs extraction of regions of interest on the face; identification logic that provides identification of differences in the regions of interest within the face; classifier logic that employs image classifiers to map the regions within the face for emotional response content; and scoring logic that evaluates the emotional response content to produce an emotion score based on the face. In addition, localization logic can further perform localization of a second face within the video, and tracking logic for tracking the first face and the second face can be utilized.

Embodiments include a computer program product embodied in a non-transitory computer readable medium for image analysis, the computer program product comprising: code for executing on a device containing image analysis logic encoded in a semiconductor chip where the code causes: evaluation logic to evaluate bodies of one or more persons in videos; localization logic to perform localization of a face within the videos where the face is from one of the bodies of the one or more persons; feature extraction logic to perform extraction of regions of interest on the face; identification logic to provide identification of differences in the regions of interest within the face; classifier logic to employ image classifiers to map the regions within the face for emotional response content; and scoring logic to evaluate the emotional response content to produce an emotion score based on the face.

Some embodiments include a processor-implemented method for analysis comprising: using a device containing image analysis logic encoded in a semiconductor chip to perform: evaluating of bodies of one or more persons in videos; localizing of a face within the videos where the face is from one of the bodies of the one or more persons; feature extraction of regions of interest on the face; identifying of differences in the regions of interest within the face; mapping, using image classifiers, the regions within the face for emotional response content; and scoring the emotional response content to produce an emotion score based on the face.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
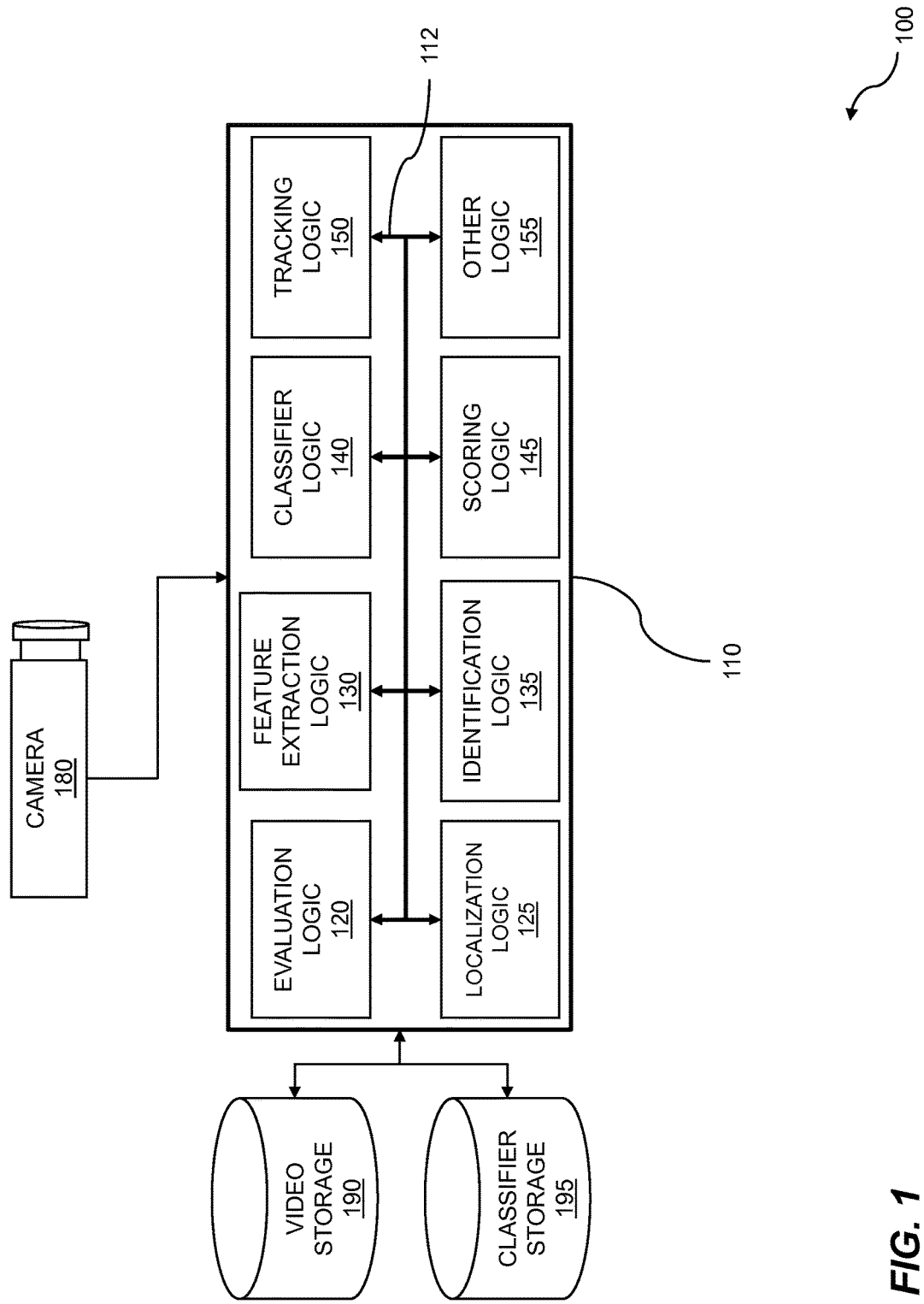
FIG. 1 is a system diagram for mental state analysis.

The proliferation of electronic devices, and handheld electronic devices in particular, has changed the ways in which people communicate. While smart phones, for example, still retain the functionality to communicate verbally, many users of these and other electronic devices often choose to communicate via other modes. For example, device users frequently choose to send SMS (text) messages, to use chat (voice and text) applications, to post on social media (e.g. Twitter™, Facebook™, Instagram™, etc.), and other "nontraditional" modes. In fact, by some reports, electronic verbal communication has become "nontraditional" in comparison to the other modes. As a result of these user driven changes in device usage, a wide variety of apps has been written. In addition, special-purpose hardware has been designed and added to the electronic devices to greatly enhance their functionality and usefulness. This special-purpose hardware supports the desired apps and usage schemes and enables new and creative additional interactions. For example, a typical smart phone today includes the battery, radios, and keyboard required to support telephony, SMS (text), and other common features, plus cameras, displays, haptic input devices (3-D touch), accelerometers, global positioning systems (GPS), audio codecs, microphones, and so on. This special-purpose hardware enables the devices to perform mapping, positioning, video communications, social networking, gaming, and other functions.

As described above, the range of mental states that people experience daily from external stimuli can effect their perceptions, responses, and reactions to the environment around them. These stimuli, which are experienced via sight, smell, touch, hearing, and taste, as well as though other senses including balance, temperature, pain, etc., can cause a person's reactions to a stimulus to change from one time of day to another, from one day to another, and so on. Furthermore, the reactions of multiple people to the same stimulus and to multiple stimuli can vary widely.

Effective communication between and among people can depend on the use of multiple senses. For example, verbal communication can be more effective when one can view the facial expressions, hand gestures, body language, and so on of the person with whom one is communicating. Facial expressions, for example, can give the listener visual cues about whether the speaker is enthusiastic about the topic of discussion, is lying or being deceptive in the conversation, is bored, and so on. As a result, self-assessment of individual emotional reactions to stimuli, including natural events, media presentations, and communication with other people, has become ubiquitous in today's social-media-saturated society. At any time, there are plentiful opportunities for an individual to assess, self-quantify, and share emotional reactions to even the most mundane of daily activities. For example, social media sites such as Facebook™, Digg™, Google+™, Meerkat™, Periscope™, Twitch™, Yelp™, and Foursquare™, among others, allow a person to instantly share his or her emotional reaction to a meal, a scenic view, a work of art, a cute puppy video, her or his partner returning from a trip, and so on, to a far-reaching audience. With the ubiquitous nature of highly mobile and web-connected devices such as smartphones, tablets, cameras, and even smartwatches and other ultra-portable wearable devices, the opportunities to share emotional reactions are prolific.

Despite the availability of numerous opportunities, applications, and techniques to share one's mental state information whenever and to whomever one chooses, the most significant barrier to sharing remains the difficulty and time-consuming nature of self-assessment. In the following embodiments, a semiconductor device is disclosed which emotionally enables a device to employ various classifiers to provide a reliable way to evaluate and communicate an accurate representation of a user's mental state. Applications can access the semiconductor logic, send information to the semiconductor (including videos or images), and receive mental state analysis returned from the semiconductor chip. The applications, commonly referred to as apps, can be built into the semiconductor chip, loaded onto the semiconductor chip, interact with the semiconductor logic, etc. Alternatively, the apps can be loaded onto a device to which the semiconductor chip is coupled.

The disclosed semiconductor logic for emotionally enabling devices allows for the automated analysis of facial expressions, body language, and other corporeal reactions. In much the same way a friend might analyze a person's mental state quickly and with minimal conscious effort, the disclosed semiconductor performs analysis and supports sharing of the analysis results in real time across a variety of communication channels. Using advanced classifiers in consort with the cameras or other imaging devices present in the vast majority of internet-connected personal electronic devices (such as smartphones and tablets), the disclosed semiconductor allows images of a person or persons to be effectively analyzed and rendered as pertinent, sharable information. For example, the semiconductor can work in tandem with a user's smartphone to employ images or videos obtained from a front-facing camera of the smartphone in order to analyze the user's emotional state while watching or after finishing a YouTube™ video or another media presentation. The smartphone can use the disclosed semiconductor chip in combination with various apps to obtain images of the user and to then evaluate a user's mental state. The user's mental state can then be analyzed by the app to evaluate different aspects of the user's mental response based on the app's intended function. If the emotional reaction of the user to a certain media presentation is negative, for example, the user can be presented with a dialogue asking whether the user desires to share his or her negative reaction with other people.

The sharing can comprise a pre-composed image containing an image of the user at the height of his or her emotional response placed beside or above an image of a specific point in the media and captioned: "'User X' did not enjoy watching 'video title.'" Thus, embodiments of the present disclosure present the user with a convenient and accurate way to share her or his response to a media instance. In the same manner, the user's smartphone or tablet camera can capture images of the user as the user performs daily tasks such as checking email, online banking, and logging exercise accomplishments or daily food consumption. Using the semiconductor and classifiers, an app on the user's device can analyze the images of daily tasks and determine at what point during the day the user had the most positive emotional response. The app can then present the user with a dialogue, first asking, "Were you browsing 'x' website at 2:34 p.m.?" If the user answers in the affirmative, another dialogue can ask, "Would you like to share the following image on a social media site?" accompanied by a pre-composed image of the user at the height of his or her emotional response and a caption such as, "'X user' was happiest today when 'X user' was browsing 'Y website' at 2:34 p.m." The app can also listen for a specific emotional event, and when the event is detected use the semiconductor chip to perform analysis on images in order to create usable mental state information pertaining to the time at which the event was detected.

The semiconductor allows the personal electronic devices of a user to be emotionally enabled. The semiconductor also allows for both the efficient transfer of mental state information between applications and the effective analysis of images. Apps or other user interfaces on the device can then use the mental state information acquired through the transfer to conveniently present individuals with various opportunities to fluidly and intuitively share and understand personal moods, emotions, and emotional states. The logic allows the user to be presented with his or her emotional states in a variety of ways. The user can thus avoid the cumbersome and often overwhelming task of subjectively analyzing and sharing emotional states and moods.

Images of one or more individuals whose mental states are sought can be collected in order to facilitate the generation of mental state data. In embodiments, images of people posting to social networks who desire to share their mental states with other social network users can be collected. The images are analyzed using one or more classifiers that can be obtained from a web service or another source. The image capture can be performed using a variety of imaging devices, including cameras on portable devices, cameras on stationary devices, and standalone cameras, provided that the imaging devices are accessible through an interface on the emotionally enabled personal electronic device or devices. Depending on the processing, storage, and communication capabilities of the emotionally enabled device, the interface allows some or all processing of the images to be performed locally on the device using the semiconductor chip.

Having obtained one or more images of an individual through an interface on a device, an evaluation of the images is performed. Similarly, one or more images can be obtained from a plurality of people using interfaces on one or more devices. The image evaluations provide insight into the mental states of the users. All or part of the image evaluation can take place on a portable device. Through evaluation, many different mental states can be determined, including frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. Other mental states can be determined through similar evaluations. Mental state information of an individual or plurality of individuals can be processed and output on the device by the semiconductor chip. The outputted information can include text, figures, images, video, and other data relating to the mental state or states of the individuals whose images were analyzed. The mental states can be rendered on a social network for sharing with other users of the social network. A user posting a message or image to a social network can choose to include additional information with the posting, including the rendering of her or his mental state or states. The posting of a representation of an analyzed mental state of a user provides viewers of the post with a keen insight into the mental state of the user in real time.

FIG. 1 is a system diagram for image analysis in support of mental state analysis. A system 100 describes an apparatus for analysis. The system 100 includes a device containing image analysis logic encoded in a semiconductor chip 110. The semiconductor chip can be a standalone chip, a subsystem of a chip, a module of multi-chip module (MCM), and so on. The semiconductor chip can be a programmable chip such as a programmable logic array (PLA), a programmable logic device (PLD), a field programmable gate array (FPGA), a read only memory (ROM), and so on. The semiconductor chip can be a full-custom chip design. The semiconductor chip can be reprogrammed, reconfigured, etc., "on the fly", in the field, or at any time convenient to the user of the semiconductor chip. The semiconductor chip can be implemented in any semiconductor technology. The semiconductor chip 110 includes evaluation logic 120 which evaluates bodies of one or more persons in videos. The evaluating of bodies can include evaluating bodies in an image, where the image can be a still image, a video, a video clip, a frame from a video, and so on. The semiconductor chip 110 includes localization logic 125 that performs localization of a face within the videos where the face is from one of the bodies of the one or more persons. The localization of the face can include any of a variety of signal and image processing techniques. The localization of the face can be accomplished using sliding a window or another technique, as used by the semiconductor device and passed across an image from the videos, in order to perform the localization. The window can include a window of any size and shape appropriate to the localization. The semiconductor chip 110 includes feature extraction logic 130 that performs extraction of regions of interest on the face. The extraction of regions of interest on the face can include extracting features such as a forehead, eyebrows, ears, eyes, a nose, cheeks, a mouth, a chin, and so on. The extraction of regions can be based on one or more of texture, shape, contrast, etc. The texture can include texture of skin and hair, for example. The shape can include the shape of the face, the shape of the nose and nostrils, the shape of the eyes, etc. The extraction of regions can be based on motion within the face. Motion within the face can comprise, for example, eye blinks, eyebrow furls and unfurls, smiles, frowns, etc.

The semiconductor chip 110 includes identification logic 135 that provides identification of differences in the regions of interest within the face. The differences in the regions of interest within the face can be used for tracking the features of the face, looking for differences among images of the same face, comparing the face to a standard facial image, comparing the face to other faces, and so on. The identification of differences in regions can be based on a histogram of gradient (HoG) evaluation. Any data representation technique can be used. The identification of differences can include evaluation of eyebrow locations. The evaluated eyebrow locations can be used to determine eyebrow raises, eyebrow furls, and so on. The identification of differences can include evaluation of eye locations. The evaluated eye locations can be used to set landmarks for eyes within the previously localized face. The eye locations can be used to track eye movements, eye direction, gaze direction, head turns, head tilts, etc. The identification of differences can include evaluation of mouth locations. The evaluated mouth locations can be used to determine expressions including smiles, frowns, neutral expressions, and so on. The identification of differences can include landmark detection within the face. The detected facial landmarks can include an outer edge of a nostril, the border of the lips, the corners of the mouth, a midpoint between the eyes, etc. A Gabor filter can be utilized in the identification of differences. The Gabor filter can be used to detect edges, where the edges can include edges of regions of interest within the face, for example.

The semiconductor chip 110 includes classifier logic 140 that employs classifiers to map the regions within the face for emotional content. The classifiers can be used to classify mapped regions of the face into emotions, mental states, moods, and so on. The classifiers can be programmed into the semiconductor chip, loaded by a user of the chip, downloaded from the Internet, and so on. The classifiers can be based on statistical classifiers that include Bayesian classifiers. In embodiments, the classifiers can be light classifiers. Light classifiers can perform some classification on the semiconductor chip and work in coordination with off-chip hardware, off-chip software, and so on. For example, classifiers used by the classifier logic can be used to perform all, little, or no classification on-chip, and the semiconductor chip can work in coordination with a server. The server, for example, can be used to perform some or all of the image analysis including image analysis using classifiers. Any analysis by the server can be performed in real-time, at a later time, and so on. The mental states can include one or more of stress, sadness, anger, happiness, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity. The classifier logic can identify deviations from a baseline facial expression. The deviations from a baseline facial expression can indicate an individual's emotions and mental states. For example, suppose that several faces are localized within a video. In this case, a deviation can include a difference in the facial expression of one face in comparison to the expressions of the other faces. However, note that a deviation can also include differences in the same facial expression. For example, the deviation can include an intensity of a smile or frown that differs by a set magnitude from a predetermined baseline.

The semiconductor chip 110 includes scoring logic 145 that evaluates the emotional content in order to produce an emotion score based on the captured face. The emotion score can be based on reactions to a series of emotion-based presentations, for example. The emotion score can be based on the alignment of responses to a baseline, including attunement to social norms, in some cases. The emotion score can be based on various parameters including self-awareness, social skill, and empathy, for example. The emotion score can include an emotion, an intensity of the emotion, and so on. The emotion score can provide information on happiness based on the regions of the face, including a mouth, such as where the mouth is smiling. Similarly, the emotion score can provide information on other emotions including sadness, agitation, irritation, confusion, and so on. The emotion score can provide information on concentration based on the regions of the face, including eyebrows, such as where the eyebrows are furrowed. The emotion score can provide information on other emotions, including surprise based on the eyebrows being raised. The device can further perform smoothing of the emotion score. Analysis of the emotion score can include capturing important patterns in the emotion score. The device can further perform image correction for the videos including one or more of lighting correction, contrast correction, or noise filtering. The image correction can be based on a variety of signal and image processing techniques including high-pass filtering, low-pass filtering, cross-correlation, etc. The emotion score can be augmented by physiological information. The physiological information can include heart rate, heart rate variability, and so on. The physiological information can be gleaned from the videos of the one or more persons. The physiological information can be extracted, inferred, etc. The physiological information can also be gleaned from one or more biosensors. The biosensors can be attached to the one or more individuals and can detect physiological parameters of the individuals including heart rate, heart rate variability, respiration rate, skin temperature, skin conductivity, and so on. The emotion score can be used to track a mood of the person for whom the face was localized. The mood can include frustration, confusion, disappointment, hesitation, cognitive overload, focusing, being engaged, being attentive, boredom, exploration, confidence, trust, delight, and satisfaction. In some embodiments, the identification logic further extracts one or more histogram-of-gradient (HoG) features from the regions of interest (RoI). In embodiments, the scoring logic produces the emotion score based on the histogram-of-gradient features.

The semiconductor chip 110 includes tracking logic 150 that tracks the first face and the second face. The tracking logic can be used to track one or more features of one or more faces, where the features can include identifying eyes, eyebrows, ears, a nose, a mouth, a chin, and so on. The facial features can include identifying marks, identifying characteristics, distinguishing marks, etc. The tracking logic can provide an identifier for the first face and the second face. The identifier can be text, numbers, characters, symbols, etc., and can be generated by the device, entered by the user, downloaded from the Internet, and so on. The tracking logic can be used to track the movement (translation, rotation, tilting, etc.) of the one or more faces within a video. The movement can be determined by comparing multiple frames from a video in which the one or more faces can be identified. The tracking logic can identify that a face has left a video frame. As before, the departure of a face from a video can be determined by comparing, for example, multiple frames from a video in which the one or more faces can be identified. The tracking logic can identify that the face has returned to the video frame and can associate information previously collected about the face from before the face left the video frame. When a face has been determined to have returned to the video, any identifiers including text, numbers, characters, symbols, etc., that have been previously associated with the returned face can be reassociated with the face.

The semiconductor chip 100 includes other logic 155 that supports the semiconductor chip. For example, the other logic can provide interface support for a variety of peripherals including one or more cameras, sensors including biosensors, storage devices such as disk drives (hard drives, solid state drives, optical drives, etc.) memory, (RAM, ROM, CAM, etc.), displays (video, LCD, LED, OLED, etc.), input/output devices (keyboards, trackpads, mice, touch screens, audio, etc.), and so on. The other logic can include special purpose hardware, where the special purpose hardware can be configured to execute algorithms, for example. The other logic can be reconfigurable, where the reconfiguration can be realized by programming. The reconfiguration of the other logic can depend on algorithms, heuristics, control schemes, etc. that are stored in a storage device, entered by the user, downloaded from the Internet, and so on. The other logic supports the semiconductor chip by providing functions not supported by the other logic blocks described above.

The semiconductor chip 110 obtains videos that are streamed from a camera 180. The camera can be any type of image capture device and can include a webcam, a video camera, a still camera, a thermal imager, a CCD device, a phone camera, a three-dimensional camera, a light field camera, multiple cameras to obtain different aspects or views of a person or multiple persons, or any other type of image capture technique that allows captured data to be used in an electronic system. The videos can include video frames that can be obtained by a camera coupled to the device. The camera can be built into the device. The camera can be coupled to the device using wireless techniques including Wi-Fi, Bluetooth®, ZigBee™, etc., or using wired techniques including Ethernet, RS-242, IEEE-488™, etc.

The semiconductor chip 110 further includes video storage memory 190 coupled to the device. The storage memory can include read-write (RW) memory, a hard disk drive (HDD), an optical drive (OD), a solid-state disk drive (SDD), etc. The video storage memory 190 can store videos for analysis by the device so that the analysis can help to evaluate moods, mental states, facial expressions, etc., for people in the videos. The videos can be obtained from the camera 180, downloaded from a network, uploaded by a user, and so on. The videos can be retrieved from the video storage memory 190 for evaluation by the evaluation logic. The videos can be retrieved using wired and wireless means. The storage memory 190 can be coupled to the bus 112 of the chip, to a USB port, to a serial port, to a parallel port, or to another communications gateway. The storage memory 190 can be coupled to the chip using wireless techniques as described above.

The semiconductor chip 110 further includes classifier storage memory 195 coupled to the device. As before, the storage memory can include read-write (RW) memory, a hard disk drive (HDD), an optical drive (OD), a solid-state disk drive (SDD), etc. The classifier storage memory 195 can store classifiers that can be used for analysis by the semiconductor device. The use of the classifiers can help evaluate mood, mental states, facial expressions, and so on, of the one or more people who can be identified in the videos. The obtaining of the classifiers can take place by the classifiers being loaded, being entered by a user, being downloaded from the Internet, and so on. The classifiers can be changed at any time by reloading, reentering, re-downloading, and so on. The classifiers can be used to reprogram, reconfigure, or otherwise change or modify the chip. For example, one or more classifiers can be used to configure the other logic 155, to modify the classifier logic 140, and so on. In embodiments, the storage memory stores classifier information used by the classifier logic.

Figure 2:
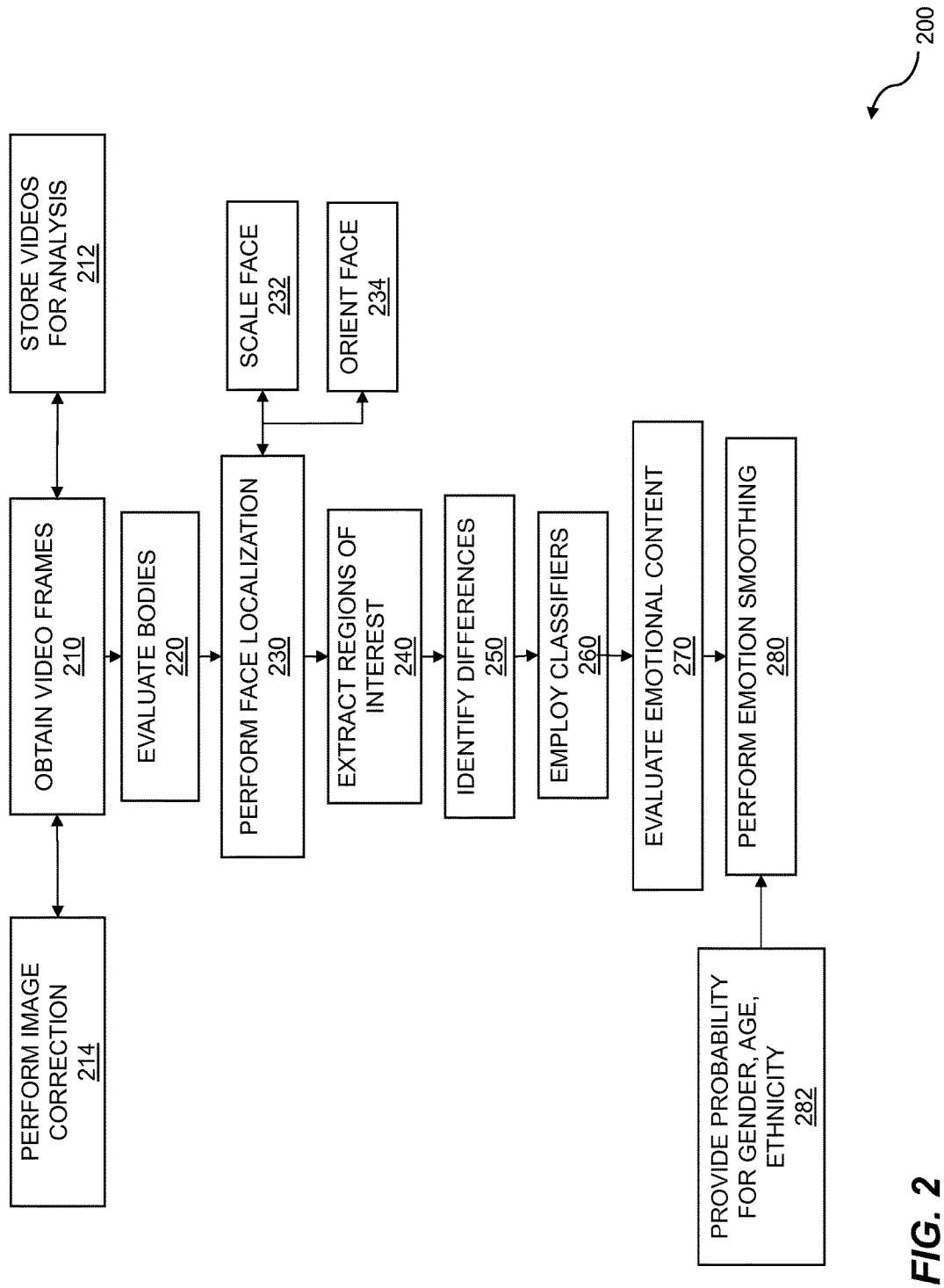
FIG. 2 is a flow diagram for mental state analysis.

FIG. 2 is a flow diagram for mental state analysis. The flow 200, or portions thereof, can be implemented in semiconductor logic. The flow 200 describes mental state analysis based on analysis of captured videos of one or more people. The flow 200 includes obtaining video frames 210 that are streamed from a camera. The video frames can be obtained from a video and can include one or more people. The camera can be any type of image capture device capable of capturing data to be used in an electronic system, such as a webcam, a video camera, a still camera, a thermal imager, a CCD device, a phone camera, a three-dimensional camera, a light field camera, multiple cameras to obtain different aspects or views of a person, or any other type of image capture technique. The flow 200 includes storing videos for analysis 212 to evaluate the moods of people in the videos. The videos can be stored in any appropriate storage medium including a hard disk drive, an optical drive, a solid state drive, and so on. The videos can be stored in cloud-based storage. The videos can be stored for later retrieval and analysis. In some embodiments, analysis of the videos is performed prior to storage. The flow 200 includes performing image correction 214 for the videos, including one or more of exposure or lighting correction, contrast correction, or noise filter smoothing. Other image corrections can be performed including highlight correction, shadow correction, saturation correction, temperature, tint, sharpness, and so on.

The flow 200 includes evaluating bodies 220 of one or more persons in videos. The videos can be partitioned into video frames, and the video frames can be evaluated for the presence of the bodies of one or more persons within the frames. When one or more persons are found to be in a frame, then further analysis of the contents of the frame can be performed. If a person is not found in the frame, then a second video frame can be obtained and evaluated. The flow 200 includes performing localization of a face 230 within the videos, where the face is from one of the bodies of the one or more persons found by the evaluation, and where the semiconductor chip performs the localization. The localization can include the localization of a plurality of faces. The localization can include selecting a region of the video frame that contains the face or faces. The localization can include scaling the face 232. The scaling of the face can include zooming in (magnifying) on the face, and zooming out (shrinking) on the face. The localization can include orienting the face 234. The orienting of the face can include rotation of the face about any axis (e.g. x, y, or z) or any combination of axes. The scaling and the orienting of the face can be performed to improve and enhance analysis of the face.

The flow 200 includes performing feature extraction of regions of interest 240 on the face. The extracting of facial features from the video can include identifying eyes, eyebrows, a nose, a mouth, a chin, ears, and so on. The flow 200 includes providing identification of differences 250 between the regions of interest within the face. For example, the identification of differences can include identifying differences in facial features of a person reacting to varying types of stimuli. The differences can include eyebrow raises, eyebrow furls, smiles, frowns, smirks, neutral expressions, etc. The flow 200 includes employing classifiers 260 to map the regions within the face for emotional content. As stated previously, the classifiers can be used to classify mapped regions of the face into emotions and mental states. The classifiers can be based on statistical classifiers, including Bayesian classifiers. The classifiers can be algorithms, heuristics, etc. The classifiers can be implemented in digital logic. The mental states can include one or more of stress, sadness, anger, happiness, frustration, confusion, disappointment, hesitation, and so on.

The flow 200 includes evaluating the emotional content 270 to produce an emotion score based on the face. The emotion score can be based on a variety of parameters. For example, the emotion score can include an emotion, an intensity value for the emotion, a probability value for the emotion, etc. The emotion score can provide information on various emotions based on the regions of the face including a mouth. For example, the mouth can be smiling, frowning, neutral, smirking, and so on, with the given position of the mouth helping to determine the emotion score. The emotion score can provide information on other emotions including sadness, agitation, irritation, confusion, happiness, etc. The flow 200 includes performing smoothing of the emotion score 280. The emotion smoothing can include various types of filtering including high-pass filtering, low-pass filtering, band-pass filtering, etc. The filtering can include noise-filtering, correlation, cross-correlation, and so on. The flow 200 includes providing the gender, age, or ethnicity of a given person in a video with an associated probability 282. Any demographic information can be provided including education level, income level, and so on. The associated probability can include error bars, a range of probabilities, and so on. Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors. Various embodiments of the flow 200 can be included on a semiconductor chip and implemented in special purpose logic, programmable logic, and so on.

Figure 3:
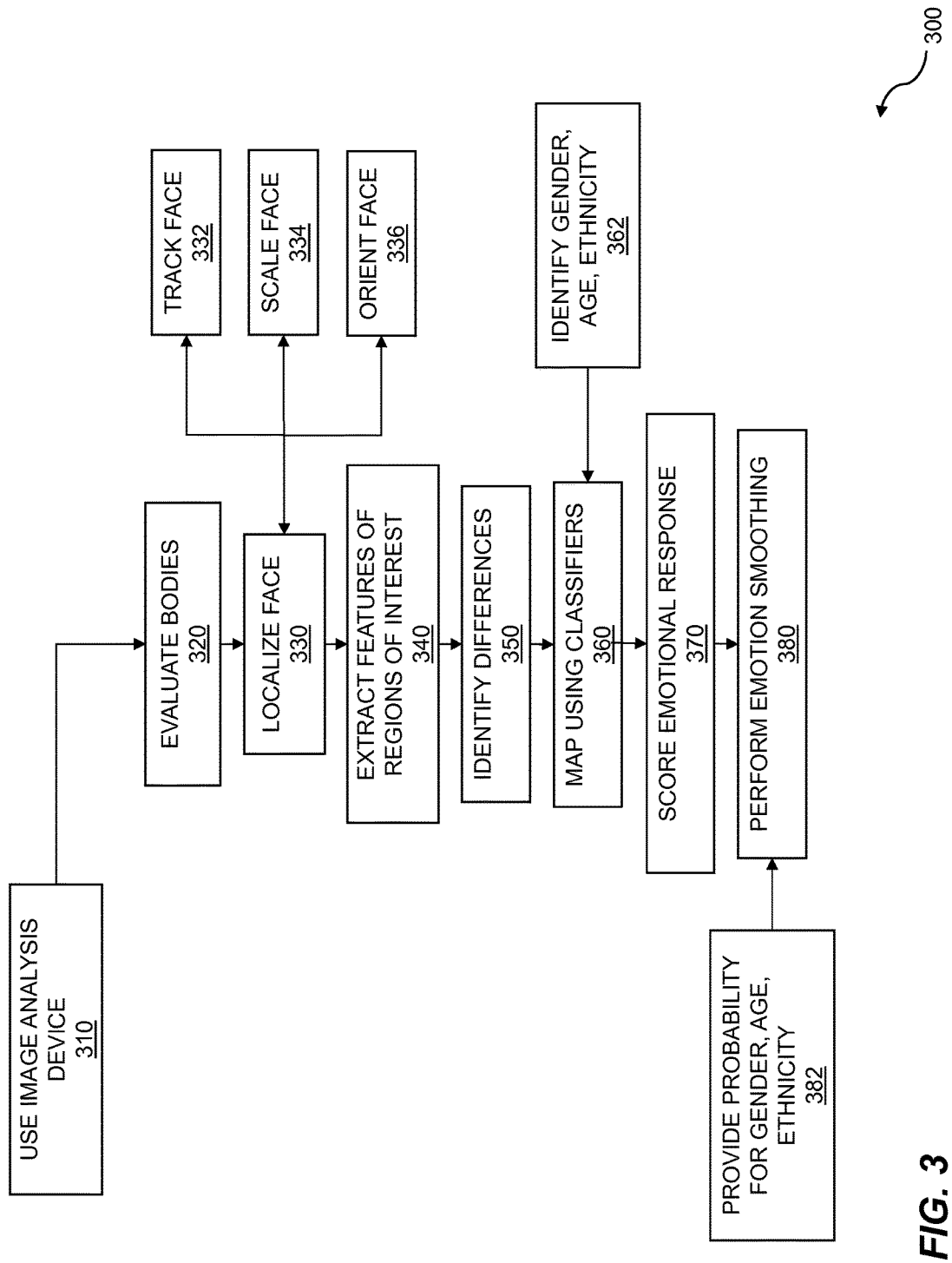
FIG. 3 is a flow diagram for image analysis device usage.

FIG. 3 is a flow diagram for image analysis device usage. The flow 300, or portions thereof, can be implemented in semiconductor logic. The flow 300 includes using an image analysis device 310 that contains image analysis logic encoded in a semiconductor chip. The semiconductor chip can be used to determine mental states by analyzing captured videos of one or more people, as previously described. The videos can include a video feed or another video source, where the video feed can be made up of video frames that can be streamed from a camera. The video frames can be extracted from a video, and the video frames can include one or more people. The camera can be any type of image capture device capable of capturing data to be used in an electronic system, such as a webcam, a video camera, a still camera, a thermal imager, a CCD device, a phone camera, a three-dimensional camera, a light field camera, multiple cameras to obtain different aspects or views of a person, or any other type of image capture technique. The flow 300 includes evaluating of bodies 320 of one or more persons in one or more videos. The analysis device can be used to determine whether one or more bodies are present within a given video frame. When one or more bodies are found, then analysis can be performed on the video frame. When no bodies are located within the given frame, the next frame can be obtained and a determination made as to whether analysis can be performed on the video frame. Recall that the absence of one or more bodies within a given frame can indicate that the one or more bodies present in a prior frame have exited the current frame. In this case, identifiers determined for a prior frame can be retained in the event that one or more bodies return in a future frame.

The flow 300 includes localizing of a face 330 within the videos, where the face is from one of the bodies of the one or more persons. The analysis device can be used to perform various algorithms and heuristics to localize a face. As discussed above, the localization of the face can be accomplished with a sliding a window or another technique. The window can include a window of any size and shape appropriate to the localization. The flow 300 further includes using the analysis device for tracking 332 the first face and the second face. As previously discussed, the analysis device can be used to track one or more features of one or more faces, where the features can include identifying eyes, eyebrows, ears, a nose, a mouth, a chin, and so on. The facial features can include identifying marks, identifying characteristics, distinguishing marks, etc. The flow 300 further uses the analysis device to perform scaling of a face 334. Scaling of the face can include zooming in (magnifying), zooming out (shrinking), and other sizing and resizing techniques. The scaling can be performed on the one or more faces that can be located in the one or more videos. The flow 300 further uses the analysis device to orient the face 336. Orienting the face can include rotation of the face about an axis (e.g. x, y, and z axes), tilting a face, and so on.

The flow 300 includes feature extraction of regions of interest on the face 340. The analysis device can be used to extract regions of interest on the face where the features can include a forehead, eyebrows, ears, eyes, a nose, cheeks, a mouth, a chin, and so on. The extraction of regions can be based on one or more of texture, shape, contrast, etc. The texture can include texture of skin and hair, for example. The shape can include the shape of the face, the shape of the nose and nostrils, the shape of the eyes, etc. The extraction of regions can be based on motion within the face. Motion within the face can comprise, for example, eye blinks, eyebrow furls and unfurls, smiles, frowns, etc. The flow 300 includes identifying of differences 350 in the regions of interest within the face. The analysis device can be used to identify the differences in the regions of interest within the face. The differences in the regions of interest within the face can be used for tracking the various features of the face. Furthermore, the differences in the regions of interest within the face can be used for looking for differences among images of the same face, comparing the face to a standard facial image, comparing the face to other faces, and so on. The identification of differences in regions can be based on a HoG evaluation, as discussed above.

The flow 300 includes mapping, using image classifiers 360, the regions within the face for emotional response content. The analysis device can use classifiers that are loaded in the device, entered by the user, downloaded from the Internet, and so on. The classifiers can be based on statistical classifiers that include Bayesian classifiers. The classifiers can be used to classify mapped regions of the face into emotions, mental states, moods, and so on. The mental states can include one or more of stress, sadness, anger, happiness, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity. The analysis device can use the classifiers, where classifiers further identify a gender, age, or ethnicity for the face 362. The gender, age, or ethnicity can be based on texture, shape, contrast, and so on. Any number of classifiers, parameters, factors, and so on, can be used to identify gender, age, or ethnicity.

The flow 300 includes scoring the emotional response 370 content to produce an emotion score based on the face. The analysis device can be used to score the emotional response, where the emotion score can be based on reactions to a series of emotion-based presentations, for example. The emotion score can be based on the alignment of responses to a baseline, including attunement to social norms, in some cases. Various parameters can be used as a basis for determining the emotion score. For example, the parameters can include self-awareness, social skill, and empathy. The emotion score can include an emotion, an intensity of the emotion, and so on. The emotion score can provide information, such as information on happiness, based on the regions of the face. The regions of the face can include a mouth where the mouth is smiling, neutral, frowning, smirking, etc. Similarly, the emotion score can provide information on other emotions including sadness, agitation, irritation, confusion, and so on. The emotion score can provide information on concentration based on the regions of the face including eyebrows, where the eyebrows are furrowed. The emotion score can provide information on other emotions including surprise, based on the eyebrows being raised.

The flow 300 includes performing smoothing of the emotion score 380. The analysis device can be used to analyze the emotion score, where the analysis can include capturing important patterns in the emotion score. The analysis device can further perform image correction for the videos including one or more of lighting correction, contrast correction, or noise filtering and smoothing of the emotion score. The image correction can be based on a variety of signal and image processing techniques including high-pass filtering, low-pass filtering, band-pass filtering, cross-correlation, etc. The flow 300 includes providing the gender, age, or ethnicity of a given person in a video with an associated probability 382. The analysis device can be used to provide any demographic information, including but not limited to education level, income level, and so on. The associated probability can include error bars, a range of probabilities, and so on. Various steps in the flow 300 may be changed in order, repeated, omitted, or the like without departing from the disclosed concepts. Various embodiments of the flow 300 may be included in a computer program product embodied in a non-transitory computer readable medium that includes code executable by one or more processors. Various embodiments of the flow 300 can be included on a semiconductor chip and implemented in special purpose logic, programmable logic, and so on.

Figure 4:
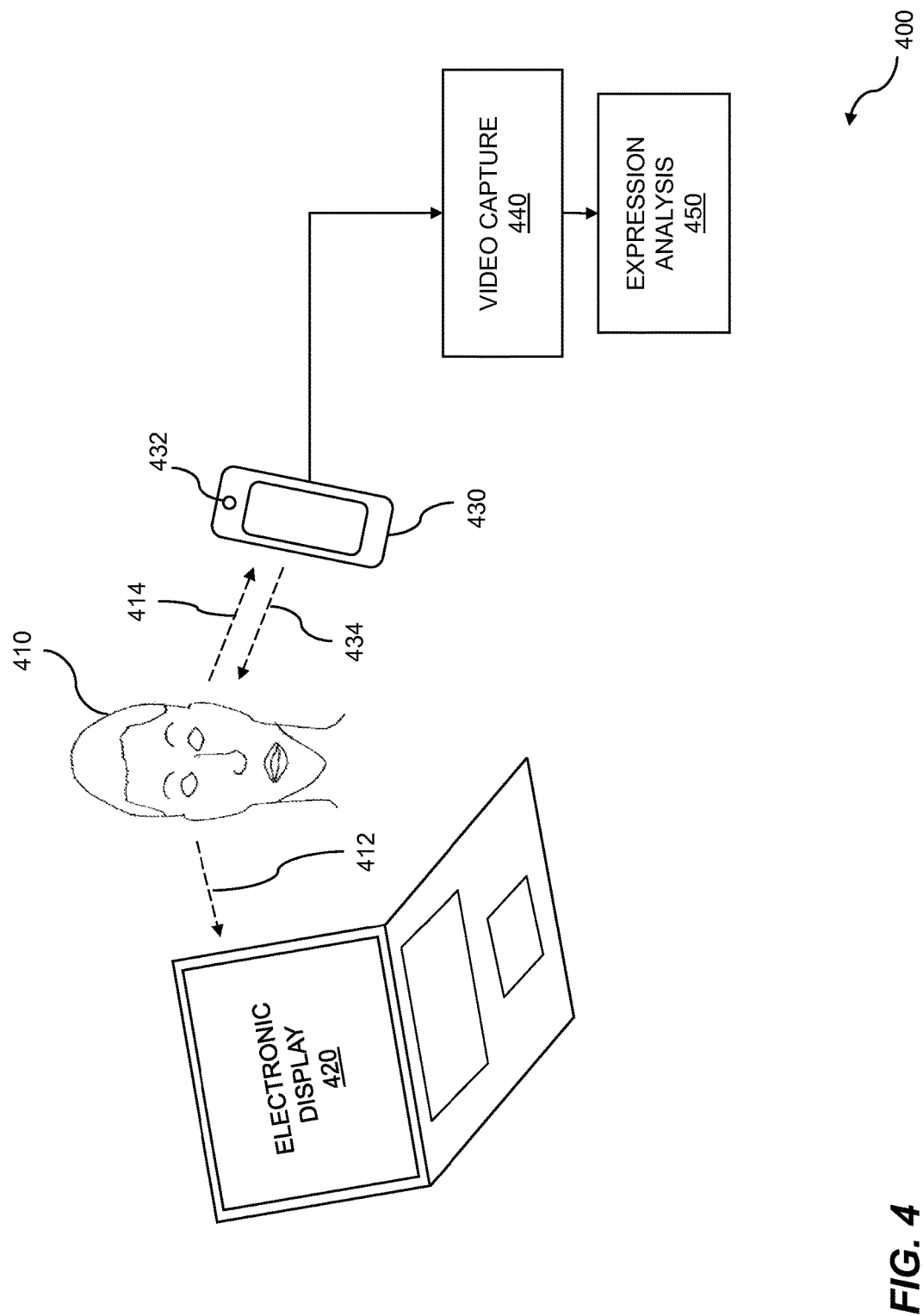
FIG. 4 is an example diagram of image collection for mental state analysis.

FIG. 4 is an example diagram of image collection for mental state analysis. The image analysis can be facilitated by semiconductor logic, such as on a mobile device 430. The example 400 shows a person 410 viewing an event on one or more electronic displays. In practice, any number of displays can be shown to the person 410. An event can be a media presentation, where the media presentation can be viewed on an electronic display. The media presentation can be an advertisement, a political campaign announcement, a TV show, a movie, a video clip, a slide show, an educational program, or any other type of media presentation. In the example 400, the person 410 has a line of sight 412 to an electronic display 420. Similarly, the person 410 also has a line of sight 414 to the display of the mobile device 430. While one person has been shown, in practical use, embodiments of the present invention analyze groups of people comprising tens, hundreds, or thousands of individuals or more. In embodiments including groups of people, each person has a line of sight 412 to the event or media presentation rendered on the digital display 420, and/or each person has a line of sight 414 to the event or media presentation rendered on a digital display of the mobile device 430. The plurality of captured videos can be of people who are viewing substantially identical media presentations or events, or conversely, the videos can capture people viewing different events or media presentations.

The display 420 can comprise a television monitor, a projector, a computer monitor (including a laptop screen, a tablet screen, a net book screen, etc.), a projection apparatus, and the like. The portable device display 430 can be a cell phone display, a smartphone display, a mobile device display, a PDA display, a tablet display, a surface display, or another electronic display. A camera can be used to capture images and video of the person 410. In the example 400, a camera 432 coupled to the mobile device 430 has a line of sight 434 to the person 410. Other cameras can be used including a webcam, a room camera, a wireless camera, etc. The webcam, for example, can be a networked digital camera that can take still and/or moving images of the face and possibly the body of the person 410. The device camera 432 can be used to capture one or more of the facial data and the physiological data.

The camera 432 coupled to the mobile device 430 can be used to capture data from the person 410. In embodiments, the camera 432 or multiple cameras are used to capture data from a plurality of people. The camera 432 can be built into the device or can be separate from but linked to the device. The camera 432 can refer to any camera, including a camera on a computer (such as a laptop, a net book, a tablet, or the like), a video camera, a still camera, a 3-D camera, a thermal imager, a CCD device, a three-dimensional camera, a light field camera, multiple webcams used to show different views of the viewers, or any other type of image capture apparatus that allows captured image data to be used in an electronic system. In addition, the camera 432 can refer to a cell phone camera as shown, a mobile device camera (including, but not limited to, a forward facing camera and a rearward facing camera), and so on. The camera 432 can capture a video or a plurality of videos of the person or persons viewing the event or situation displayed on the electronic display 420. The plurality of videos can be captured of people who are viewing substantially identical situations, such as viewing media presentations or events. The videos can be captured by a single camera, an array of cameras, randomly placed cameras, a mix of camera types, and so on. As mentioned above, media presentations can comprise an advertisement, a political campaign announcement, a TV show, a movie, a video clip, an educational program, or any other type of media presentation. The media can be oriented toward an emotion. For example, the media can include comedic material to evoke happiness, tragic material to evoke sorrow, and so on.

A video capture module 440 can receive the facial data collected by the camera 432. The video data can include streamed video data, where the videos can be streamed from the camera 432. The videos can include video frames obtained by the camera 432. The video capture module 440 can decompress the video into a raw format from a compressed format such as H.264, MPEG-2, or the like. Facial data that is received can be received in the form of a plurality of videos, with the plurality of videos coming from a plurality of devices, cameras, etc. The plurality of videos can be of one person and/or of a plurality of people who are viewing substantially identical situations or substantially different situations. The facial data can include information on action units, head gestures, eye movements, muscle movements, expressions, smiles, and the like.

The raw video data can then be processed for expression analysis 450. The processing can include analysis of expression data, action units, gestures, mental states, and so on. Facial data as contained in the raw video data can include information on one or more of action units, head gestures, smiles, brow furrows, squints, lowered eyebrows, raised eyebrows, attention, and the like. The action units can be used to identify smiles, frowns, and other facial indicators of expressions. Gestures can also be identified, such as a head tilt to the side, a forward lean, a smile, a frown, as well as many other gestures. Other types of data including physiological data can be obtained, where the physiological data can be obtained through the camera 432 without contacting the person or persons. Respiration, heart rate, heart rate variability, perspiration, temperature, and other physiological indicators of mental state can be determined by analyzing the images and the video data. All of this analysis can be implemented and performed, or augmented by, semiconductor logic.

Figure 5:
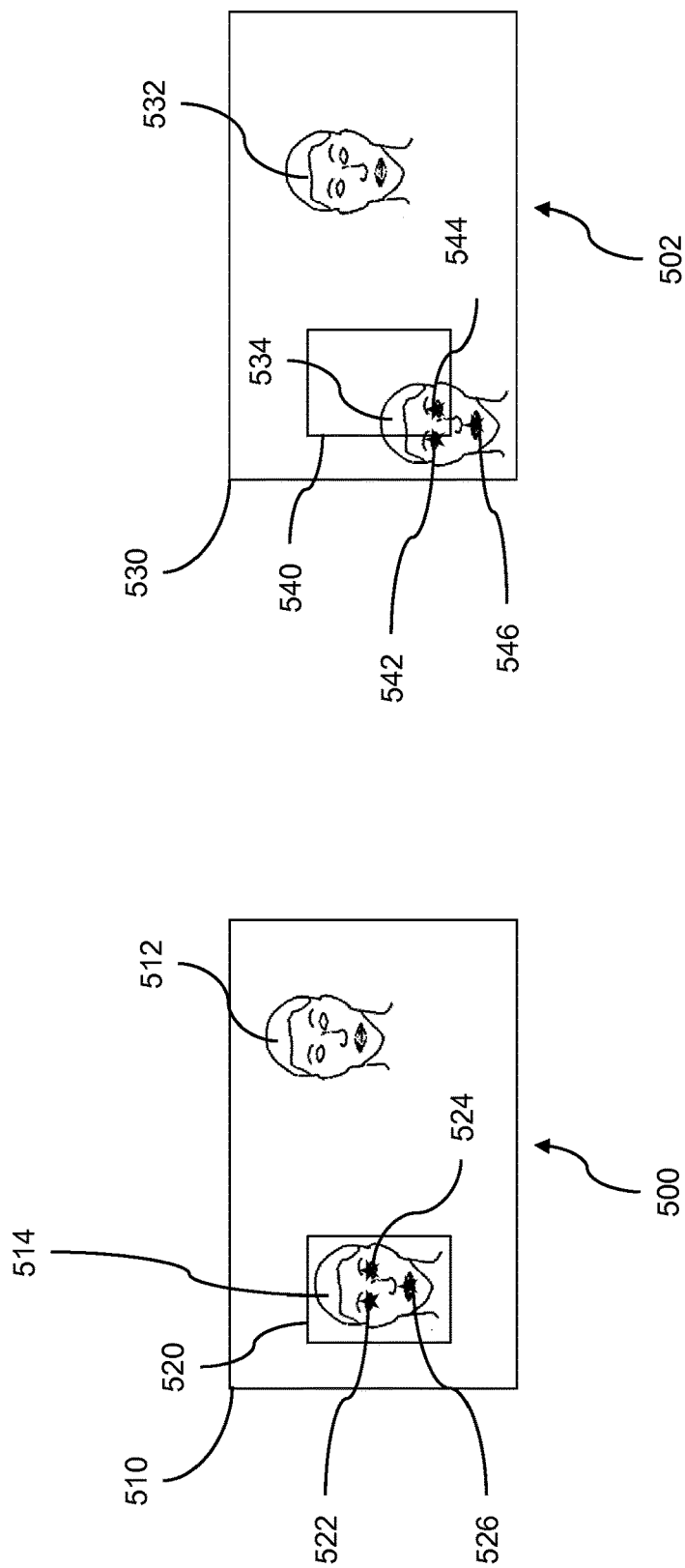
FIG. 5 is an example illustrating a second face.

FIG. 5 shows an example illustrating a second face and associated detection. Such detection and analysis can be performed by semiconductor logic. The analysis device can be used to perform face detection for a second face, as well as facial tracking One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, for example, by analyzing a known set of data, known as a training set. The training set can include data for which category memberships of the data can be known. The training set can be used as part of a supervised training technique. If a training set is not available, then a clustering technique can be used to group observations into categories. This latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. For example, classification of one or more observations into one or more groups can be based on distributions of the data values, probabilities, and so on. Classifiers can be binary, multiclass, linear and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 5, the detection of the second face can include identifying facial landmarks, generating a bounding box, and prediction of a bounding box and landmarks for a next frame, where the next frame can be one of a plurality of frames of a video containing faces. A first video frame 500 includes a boundary 510, a first face 512, and a second face 514. The frame 500 also includes a bounding box 520. Facial landmarks can be generated for the first face 512. Face detection can be performed to initialize a second set of locations for a second set of facial landmarks for a second face within the video. Facial landmarks in the video frame 500 can include the facial landmarks 522, 524, and 526. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face, and can include estimating a second rough bounding box for the second face based on the facial landmark detection. For example, the estimating of a second rough bounding box can include the bounding box 520. Bounding boxes can also be estimated for one or more other faces within the frame 510. The bounding box can be refined, as can one or more facial landmarks. The refining of the second set of locations for the second set of facial landmarks can be based on localized information around the second set of facial landmarks. The bounding box 520 and the facial landmarks 522, 524, and 526 can be used to estimate future locations for the second set of locations for the second set of facial landmarks in a future video frame from the first video frame.

A second video frame 502 is also shown. The second video frame 502 includes a frame boundary 530, a first face 532, and a second face 534. The second frame 502 also includes a bounding box 540 and the facial landmarks 542, 544, and 546. In other embodiments, any number of facial landmarks are generated and used for facial tracking of the two or more faces of a video frame, such as the shown second video frame 502. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, any number of facial points can be determined within a frame. One or more of the other facial points that are determined can correspond to a third face. The location of the bounding box 540 can be estimated, where the estimating can be based on the location of the generated bounding box 520 shown in the prior frame 500. The three facial points shown, facial points 542, 544, and 546, might lie within the bounding box 540 or might not lie partially or completely within the bounding box 540. For example, the second face 534 might have moved between the first video frame 500 and the second video frame 502. Based on the accuracy of the estimating of the bounding box 540, a new estimation can be determined for a third, future frame from the video, and so on. The evaluation can be performed, all or in part, on semiconductor based logic.

Figure 6:
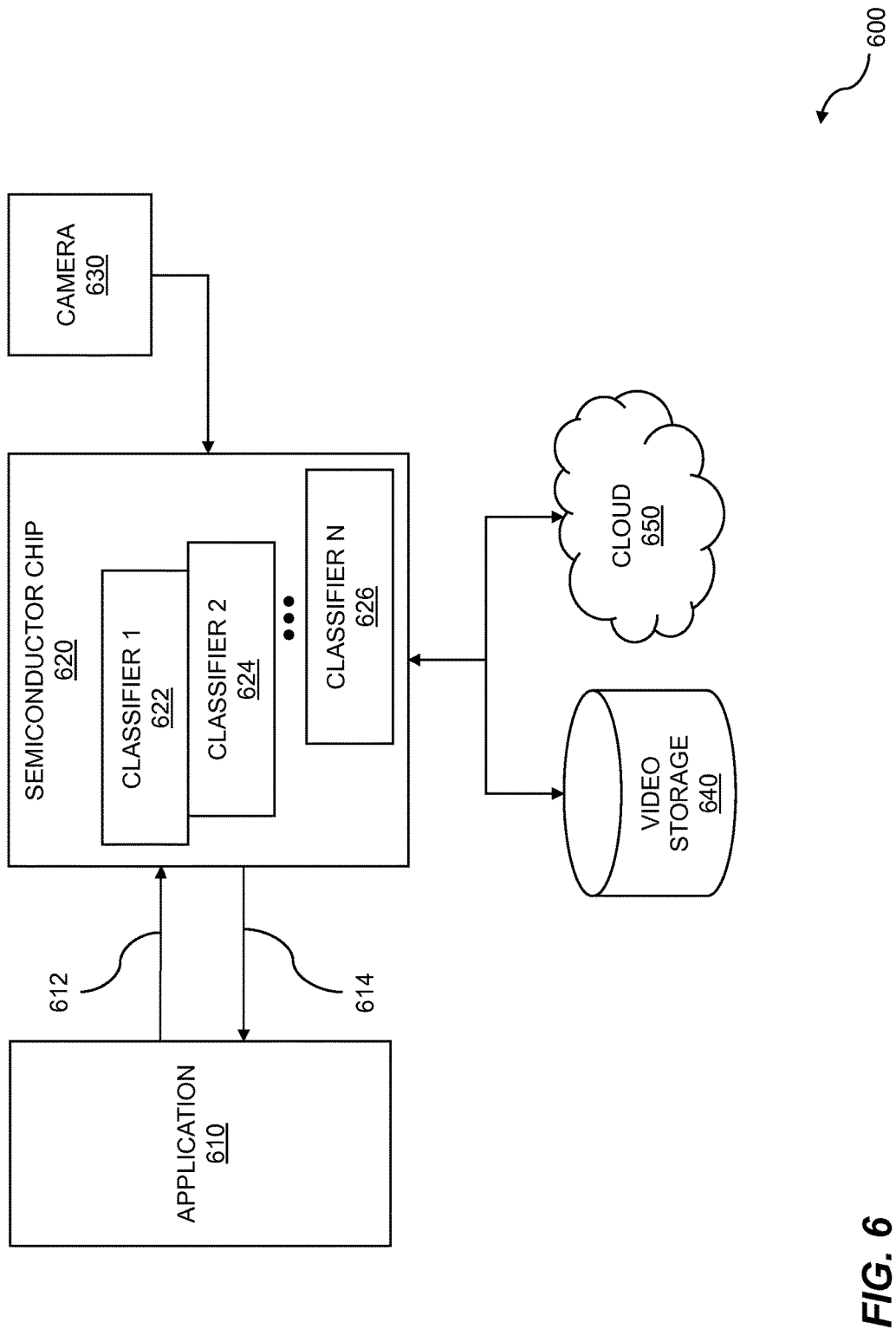
FIG. 6 is an example diagram of a semiconductor chip with classifiers.

FIG. 6 is an example diagram of a semiconductor chip with classifiers. In the diagram 600, an application 610, hereafter referred to as an app, is shown loaded onto a device. The device can be any of a range of devices, including portable devices such as laptop computers and ultra-mobile PCs; mobile devices such as smartphones, PDAs, and tablets; and wearable devices such as glasses and wrist watches, etc. Any number of apps can be loaded or running on the device. The apps can include a social networking app, such as Facebook™, Digg™, Google+™, LinkedIn™, Tumblr™, Foursquare™, Yelp™, and so on. Numerous other types of apps can likewise utilize emotional enablement. Emotional enablement of an app can allow a user to automatically express her or his emotions while using the app. In many cases, the devices contain built-in cameras, but some devices might employ external cameras that are connected to the device, accessible by the device, and so on.

In the example shown, an app 610 communicates with a semiconductor chip 620 which allows for emotionally enabling the app. In some embodiments, the semiconductor chip is a stand-alone chip, a custom chip, an FPGA, a module included in a chip, and so on. The semiconductor chip 620 shown includes multiple classifiers to process mental state data and infer mental states. The classifiers can be employed to map the regions within a face for emotional content. The mental states can include one or more of stress, sadness, anger, happiness, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity. One or more mental states can be analyzed to determine emotional states, moods, and other useful information which can prove difficult for an individual to self-identify. In embodiments, one or more classifiers are present in a semiconductor chip. In the figure shown, three example classifiers are present: classifier 1 622, classifier 2 624, and classifier N 626. While classifiers are typically code or data from a cloud or another remote source, classifiers can be stored locally on the semiconductor chip in some cases. In embodiments, any number of classifiers are possible. The classifiers can be obtained from any of a variety of sources, including by Internet download, from an application vendor site, from user-developed code, and so on. Similarly, new classifiers can be obtained from a variety of sources. The classifiers in the semiconductor chip can be updated automatically. The classifiers can be used to identify deviations from a baseline facial expression. The baseline facial expression can be a standard facial expression, a typical facial expression for a person, and so on.

Various communication channels can exist between an app and the semiconductor chip. For example, the app 610 can communicate with the semiconductor chip 620 via a channel 612 and can receive a communication back from the semiconductor chip via the same channel or another channel, such as a second channel 614. The semiconductor chip 620 can receive an initialization instruction or another communication through the channel 612 from the app 610. The semiconductor chip can perform various operations based on the initialization. The operations performed can include one of more of the classifiers 1 622 through N 626. The operations performed can include mapping the regions within the face for emotional content and evaluating the emotional content to produce an emotion score based on the face and the mapped regions. Information on the one or more emotional states, on the mapping of the regions within the face for emotional content, on the evaluating the emotional content to produce an emotion score, etc., can be returned to the app 610 using the second channel 614.

The semiconductor chip 620 can use classifiers to process and analyze mental state data gathered from a user or users. In embodiments, the data is in the form of an image or video of the user or users. The image or video can be obtained from a variety of sources, including one or more cameras 630, video file storage systems 640, or cloud-based resources 650, and can be obtained using a variety of networking techniques, including wired and wireless networking techniques. In embodiments, the images are from a collection of photographs, an album, or another grouping of images or videos. The application can pass parameters or information on the source of the video or images that contain mental state data to the semiconductor chip. Mental state information, when analyzed from the mental state data, can aid individuals in identifying emotional states and moods. In embodiments, the app 610, semiconductor chip 620, camera 630, and video file storage systems 640 reside on the same device.

The classifiers 622, 624, and 626 can be utilized by support vector machine analysis to identify the emotional content. The support vector machine can be used for machine learning. The support vector machine can include supervised learning models and learning algorithms and can be used to analyze the emotional content for the classification. The support vector machine can use a pre-trained algorithm. The algorithm can be used to identify the emotional contact. In some embodiments, the pre-trained algorithm serves as a starting point in the machine learning and can be modified to improve identification of the emotional content. The support vector machine can generate the emotion score. The emotion score can be used by a software application running on a processor coupled to the device or semiconductor chip 620. In embodiments, the emotion score can be used directly by accessing special hardware included in the semiconductor chip 620. In some embodiments, the classifiers on the semiconductor chip can be a lighter or simpler version that can assist in sifting image data. Then a fuller set of classifiers can be performed on web-based servers, if warranted.

Figure 7:
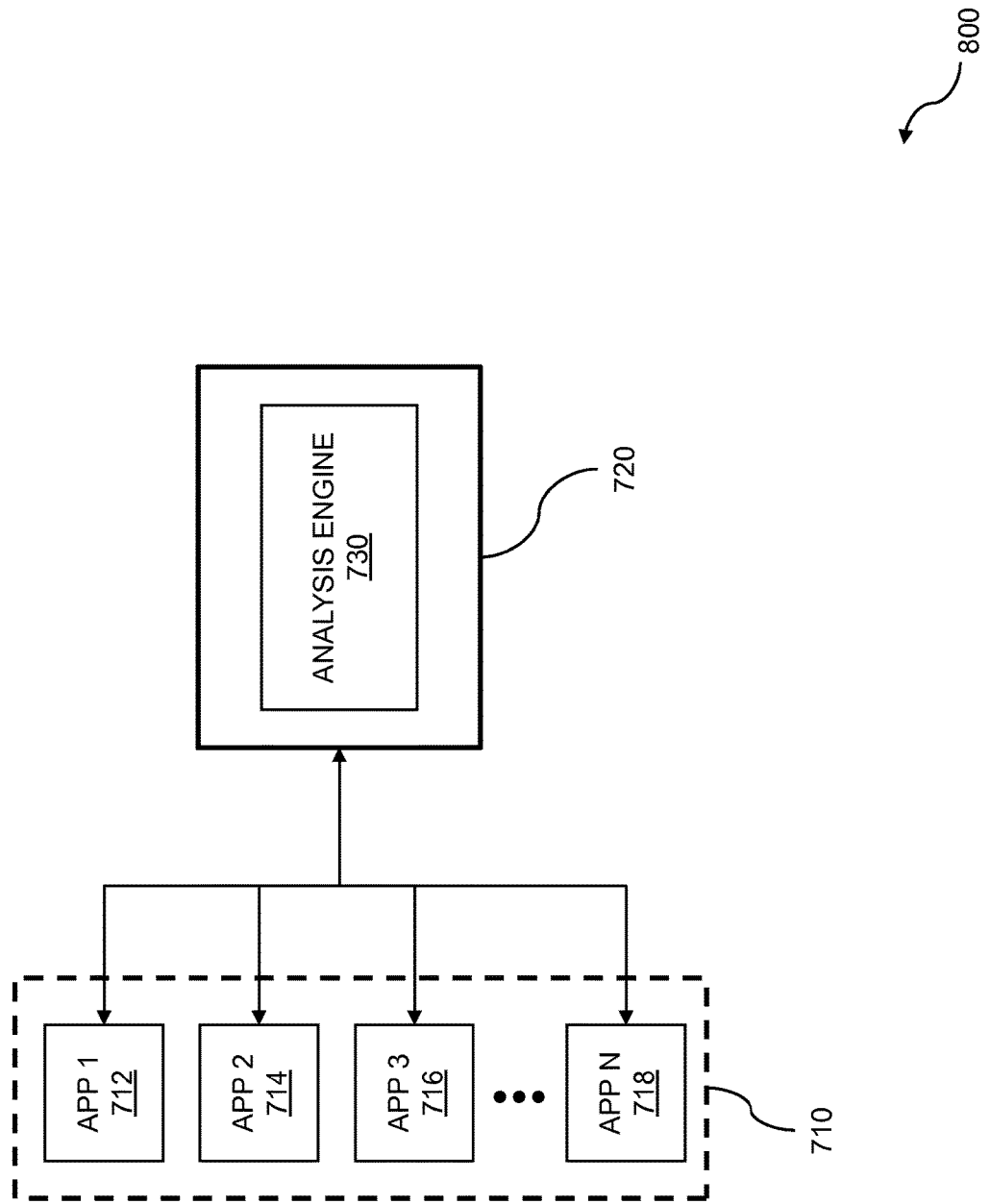
FIG. 7 is an example diagram of apps calling the semiconductor chip analysis engine.

FIG. 7 is an example diagram of software apps calling logic on a semiconductor chip. In the example 700, one or more apps 710 call a semiconductor chip 720. The apps can reside on a device, where the device can be a portable device such as a laptop or ultra-mobile PC; a mobile device such as a smartphone, tablet, or surface; a wearable device such as glasses or a watch; and so on. In embodiments, the apps 710 and the semiconductor chip 720 reside on the same device. The apps 710 can include a single app, such as an app 1 712. In some embodiments, the apps 710 comprise a plurality of applications, such as the app 1 712, an app 2 714, an app 3 716, an app N 718, and so on. The apps can comprise any of a variety of apps, including social media apps. The semiconductor chip 720 can provide emotional enablement to a device on which the semiconductor chip 720 resides. A user can choose to emotionally enable any number of apps loaded on her or his device. The one or more apps 710 can send video, images, raw data, or other user information to the semiconductor chip 720 for analysis. The images, video, user information, and the like can be generated by the device, obtained by the device, loaded onto the device, and so on.

The semiconductor chip 720 can include analysis capabilities in the form of an analysis engine 730. In some embodiments, the semiconductor chip 720 also communicates with other devices and services, including a web service. Analysis of raw data can be performed on the device, on the web service, or on both. The raw data can include images, video, video clips, user information, and so on. In at least one embodiment, all of the analysis needed by the one or more apps 710 is performed on the device. The analysis engine 730 can analyze the image or video to determine one or more mental states, where the mental states can include one or more of stress, sadness, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity. The analysis engine 730 can determine one or more emotional states based on the mental state information. The analysis engine 730 can employ classifiers to map the regions within a face for emotional content. The classifiers can include facial expressions such as happy, sad, angry, fearful, etc., as well as information such as race, gender, and so on. The classifiers can map facial regions including the mouth, eyes, eyebrows, etc. The analysis engine can evaluate emotional content to produce an emotion score based on the face. The emotion score can be used by a software application running on a processor coupled to the device or semiconductor chip 720. In another embodiment, a hardware module coupled to the semiconductor chip 720, or incorporated into the chip, can use the emotion score. The emotion score can be used to rank the intensity of the facial expressions, for example.

Figure 8:
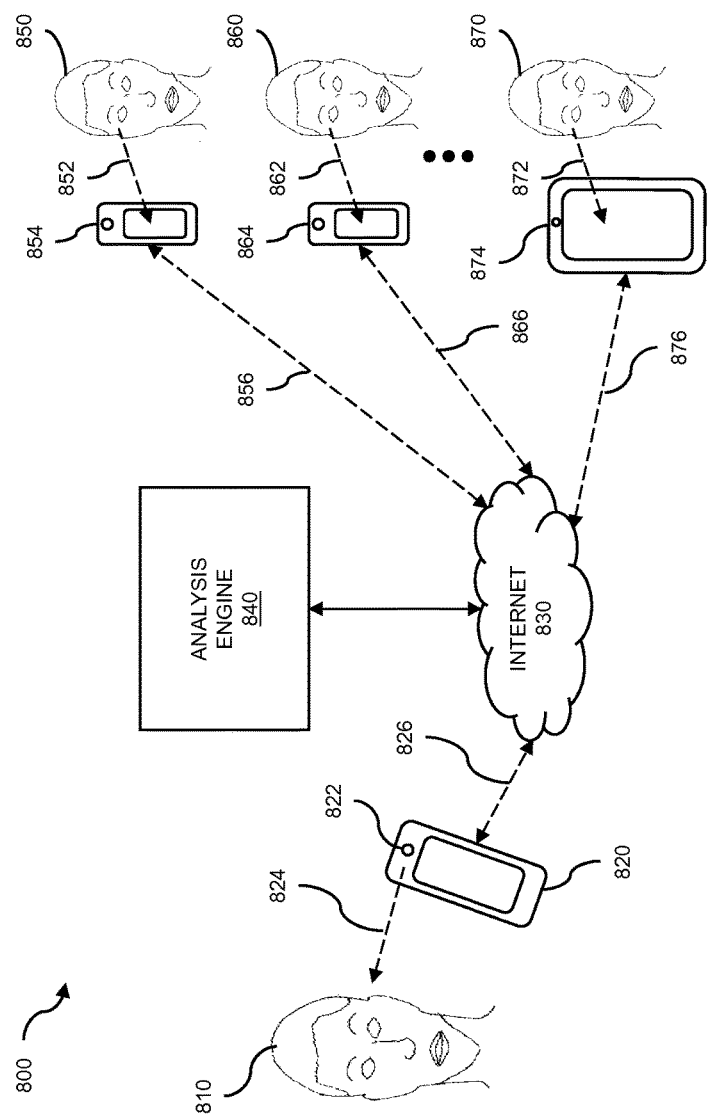
FIG. 8 is an example illustrating streaming of social video.

FIG. 8 is an example illustrating streaming of social video. The streaming and analysis can be facilitated via semiconductor based logic. The streaming can be live-streaming. Such streaming can include mental state event signature analysis. Live-streaming video is an example of one-to-many social media, where video can be sent over the Internet from one person to a plurality of people using a social media app and/or platform. Live-streaming is one of numerous popular techniques used by people who want to disseminate ideas, send information, provide entertainment, share experiences, and so on. Some of the live-streams can be scheduled, such as webcasts, online classes, sporting events, news, computer gaming, or videoconferences, while others can be impromptu streams that are broadcast as needed or when desirable. Examples of impromptu live-stream videos can range from individuals simply wanting to share experiences with their social media followers, to live coverage of breaking news, emergencies, or natural disasters. The latter coverage can be known as mobile journalism, or "mo jo", and is becoming increasingly common. With this type of coverage, "reporters" can use networked, portable electronic devices to provide mobile journalism content to a plurality of social media followers. Such reporters can be quickly and inexpensively deployed as the need or desire arises.

Several live-streaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the live-stream can comment on the stream using tweets that can be seen by and responded to by the broadcaster. Another popular app is Periscope™ that can transmit a live recording from one user to that user's Periscope™ account and other followers. The Periscope™ app can be executed on a mobile device. The user's Periscope™ followers can receive an alert whenever that user begins a video transmission. Another live-stream video platform is Twitch™ that can be used for video streaming of video gaming and broadcasts of various competitions and events.

The example 800 shows a user 810 broadcasting a video live-stream to one or more people 850, 860, 870, and so on. A portable, network-enabled electronic device 820 can be coupled to a forward-facing camera 822. The portable electronic device 820 can be a smartphone, a PDA, a tablet, a laptop computer, and so on. The camera 822 coupled to the device 820 can have a line-of-sight view 824 to the user 810 and can capture video of the user 810. The captured video can be sent to an analysis or recommendation engine 840 using a network link 826 to the Internet 830. The network link can be a wireless link, a wired link, and so on. The recommendation engine 840 can recommend to the user 810 an app and/or platform that can be supported by the server and can be used to provide a video live-stream to one or more followers of the user 810. In the example 800, the user 810 has three followers: the person 850, the person 860, and the person 870. Each follower has a line-of-sight view to a video screen on a portable, networked electronic device. In other embodiments, one or more followers follow the user 810 using any other networked electronic device, including a computer. In the example 800, the person 850 has a line-of-sight view 852 to the video screen of a device 854; the person 860 has a line-of-sight view 862 to the video screen of a device 864, and the person 870 has a line-of-sight view 872 to the video screen of a device 874. The portable electronic devices 854, 864, and 874 can each be a smartphone, a PDA, a tablet, and so on. Each portable device can receive the video stream being broadcast by the user 810 through the Internet 830 using the app and/or platform that can be recommended by the recommendation engine 840. The device 854 can receive a video stream using the network link 856, the device 864 can receive a video stream using the network link 866, the device 874 can receive a video stream using the network link 876, and so on. The network link can be a wireless link, and wired link, and so on. Depending on the app and/or platform that can be recommended by the recommendation engine 840, one or more followers, such as the followers 850, 860, 870, and so on, can reply to, comment on, and otherwise provide feedback to the user 810 using their devices 854, 864, and 874, respectively.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined, including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from any number of viewers who are online. That is, the collection of videos can be crowdsourced from those viewers who elected to opt-in to the video data collection.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include such items as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. For example, the AUs can be used to recognize emotions experienced by the observed person. Emotion-related facial actions can be identified using the emotional facial action coding system (EMFACS) and the facial action coding system affect interpretation dictionary (FACSAID), for example. For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated, as well as specific emotions, moods, or mental states.

The coding of faces identified in videos captured of people observing an event can be automated. The automated systems can detect facial Ails or discrete emotional states. The emotional states can include amusement, fear, anger, disgust, surprise, and sadness, for example. The automated systems can be based on a probability estimate from one or more classifiers, where the probabilities can correlate with an intensity of an AU or an expression. The classifiers can be used to identify into which of a set of categories a given observation can be placed. For example, the classifiers can be used to determine a probability that a given AU or expression is present in a given frame of a video. The classifiers can be used as part of a supervised machine learning technique, where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. For example, the image can be adjusted by flipping the image around a vertical line through the middle of a face in the image. The symmetry plane of the image can be determined from the tracker points and landmarks of the image.

In an embodiment, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including a symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions, and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis. This grouping and other analyses can be facilitated via semiconductor based logic.

Figure 9:
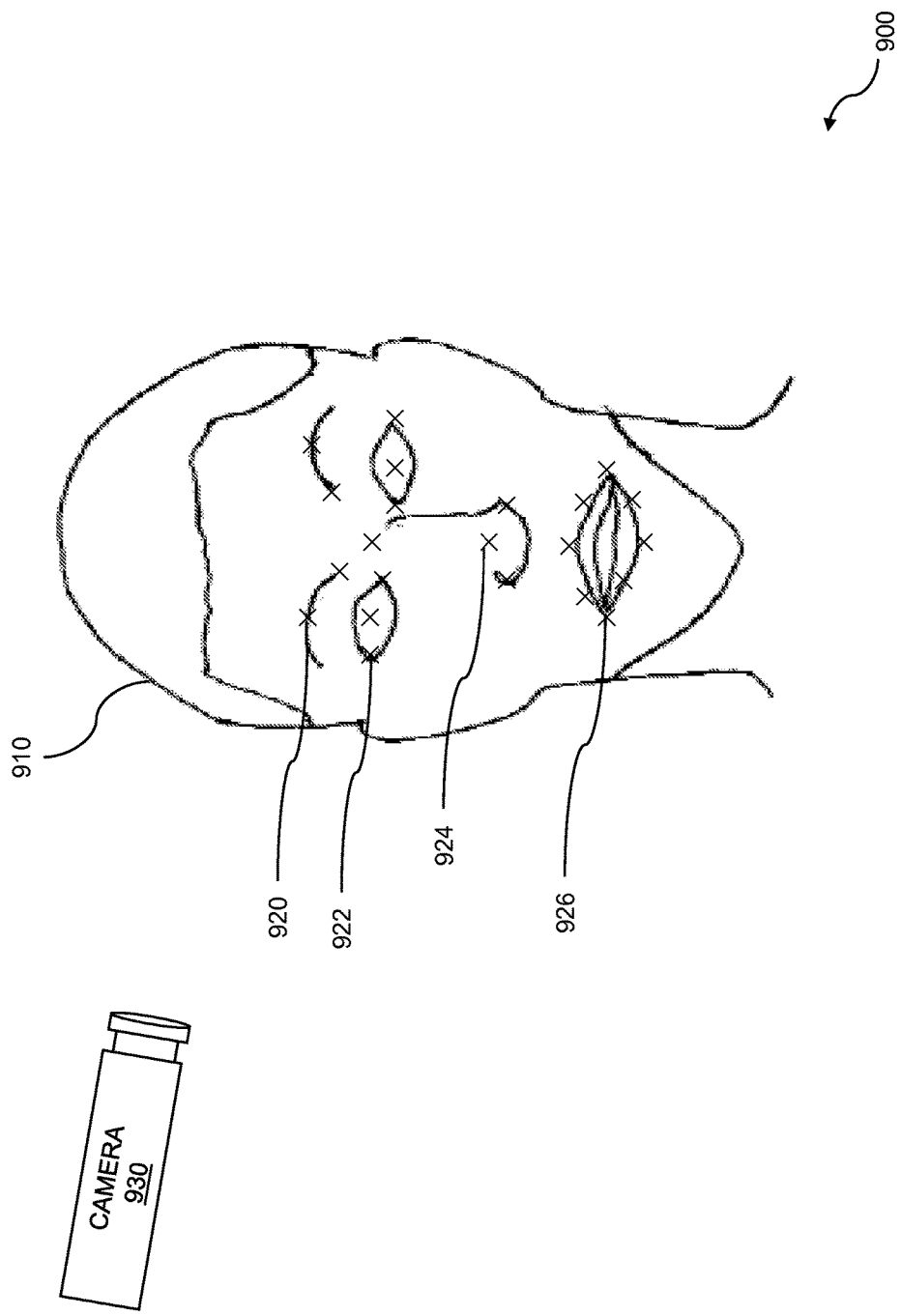
FIG. 9 shows example facial data collection including landmarks.

FIG. 9 shows a diagram 900 illustrating example facial data collection including landmarks. The analysis of landmarks can be accomplished using semiconductor implemented logic. A face 910 can be observed using a camera 930 in order to collect facial data that includes facial landmarks. The facial data can be collected from a plurality of people using one or more of a variety of cameras. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend, for example, on the position of the camera 930 relative to the face 910, the number of cameras used, the illumination of the face, etc. For example, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Any number of facial landmarks can be identified from the facial data that is captured. The facial landmarks that are identified can be analyzed to identify facial action units. For example, the action units that can be identified can include AU02 outer brow raiser, AU14 dimpler, AU17 chin raiser, and so on. Any number of action units can be identified. The action units can be used alone and/or in combination to infer one or more mental states and emotions. A similar process can be applied to gesture analysis (e.g. hand gestures) with all of the analysis being accomplished or augmented by semiconductor based logic.

Figure 10:
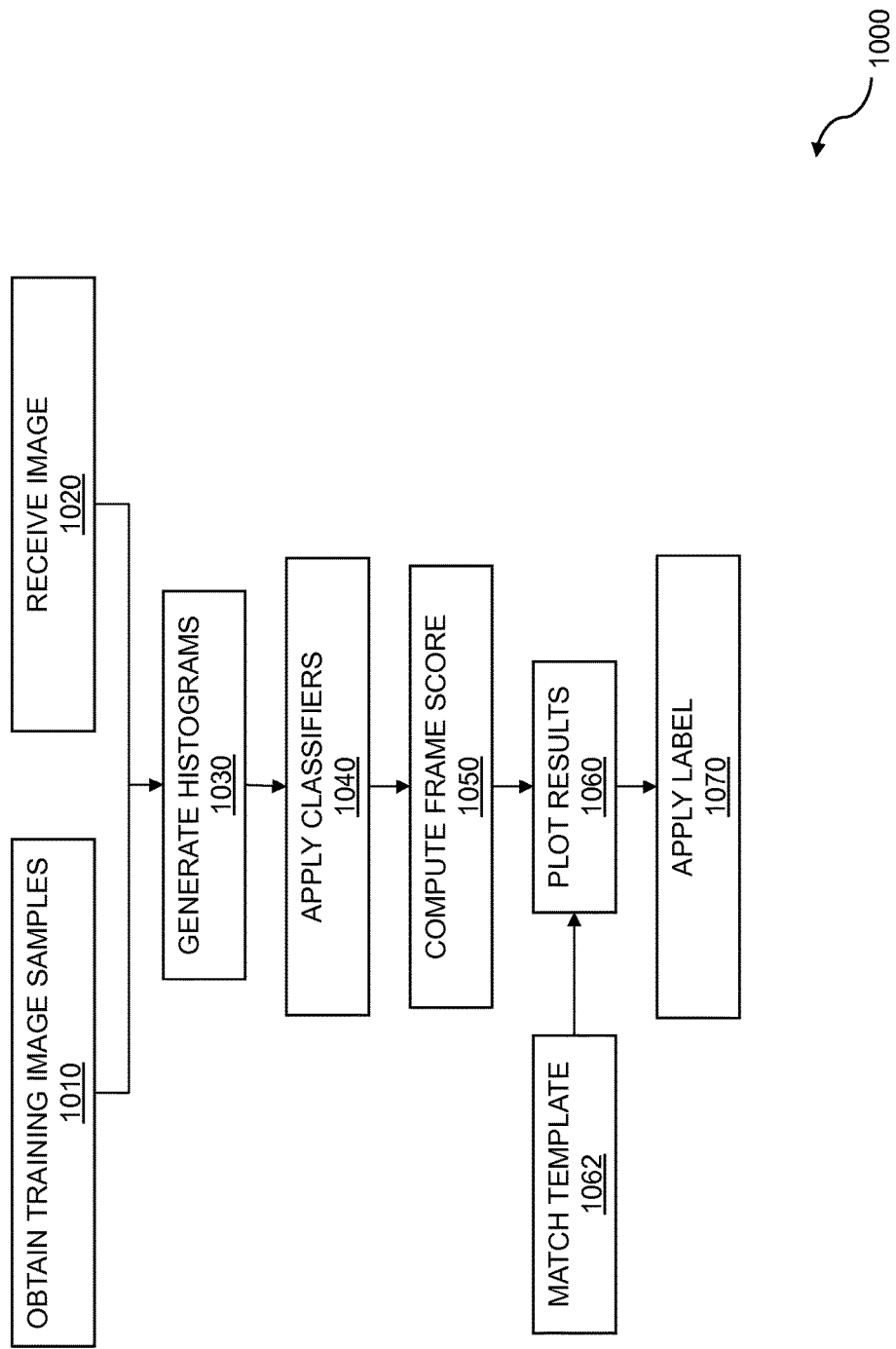
FIG. 10 is a flow for detecting facial expressions.

FIG. 10 is a flow for detecting facial expressions. This flow, or portions thereof, can be implemented in semiconductor logic. The flow 1000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU) where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1000 begins by obtaining training image samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, such as the camera 930 from FIG. 9, for example. The flow 1000 continues with receiving an image 1020. The image 1020 can be received from the camera 930. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. For example, the manipulated image and a flipped or mirrored version of the manipulated image can be analyzed alone and/or in combination to improve analysis. The flow 1000 continues with generating histograms 1030 for the training images and the one or more versions of the received image. The histograms can be generated for one or more versions of the manipulated received image. The histograms can be based on a HoG or another histogram. As described above, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example.

The flow 1000 continues with applying classifiers 1040 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. For example, the classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1000 continues with computing a frame score 1050. The score computed for an image, where the image can be a frame from a video, can be used to determine the presence of a facial expression in the image or video frame. The score can be based on one or more versions of the image 1020 or manipulated image. For example, the score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

Figure 11:
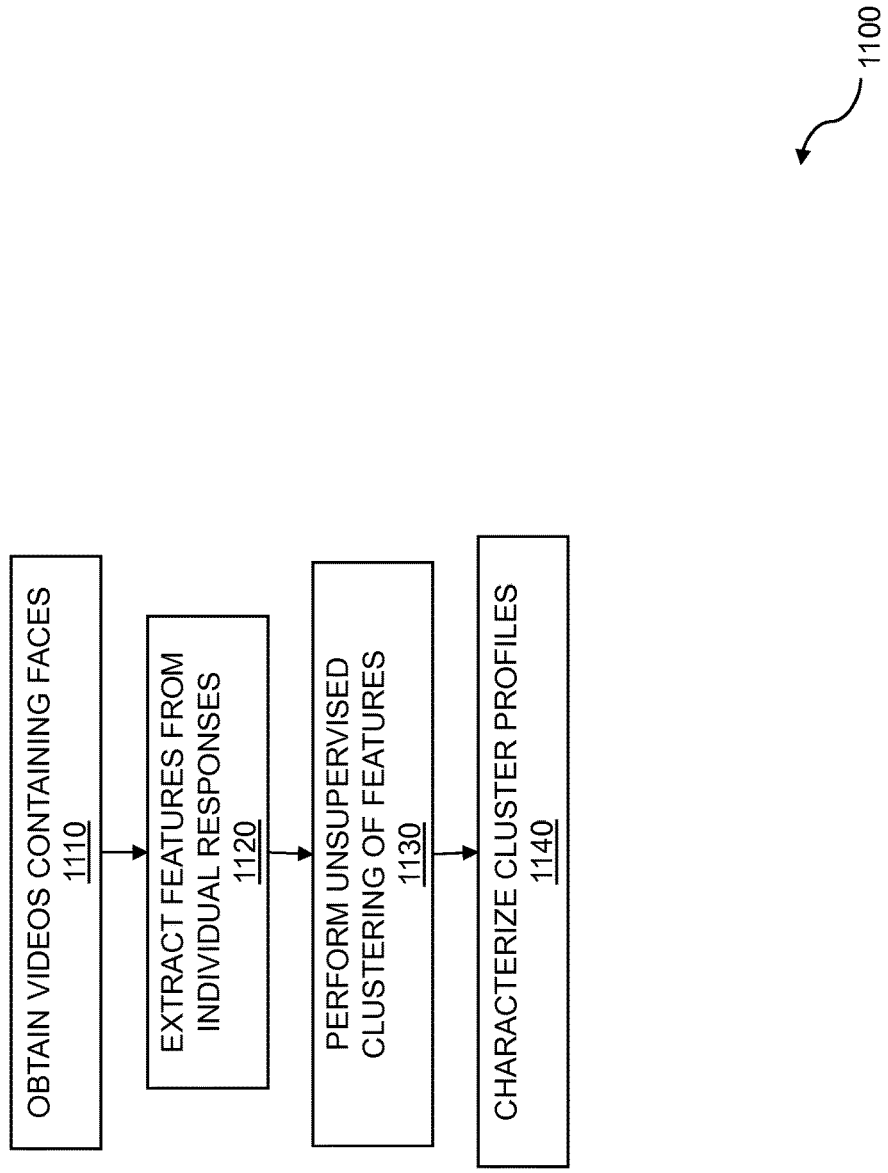
FIG. 11 is a flow for the large-scale clustering of facial events.

The flow 1000 continues with plotting results 1060. The results that are plotted can include one or more scores for one or frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image that was received 1020. For example, the label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 can be included in a computer program product embodied in a non-transitory computer readable medium that includes code executable by one or more processors. Various embodiments of the flow 1000, or portions thereof, can be included on a semiconductor chip and implemented in special purpose logic, programmable logic, and so on FIG. 11 is a flow for the large-scale clustering of facial events. The clustering and evaluation of facial events can be augmented using semiconductor based logic. As discussed above, collection of facial video data from one or more people can include a web-based framework. The web-based framework can be used to collect facial video data from, for example, large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on.

The flow 1100 begins with obtaining videos containing faces 1110. The videos can be obtained using one or more cameras, where the cameras can include a webcam coupled to one or more devices employed by the one or more people using the web-based framework. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 continues with characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. For example, the number of smiles resulting from people viewing a humorous video can be compared to various demographic groups, where the groups can be formed based on geographic location, age, ethnicity, gender, and so on.

Figure 12:
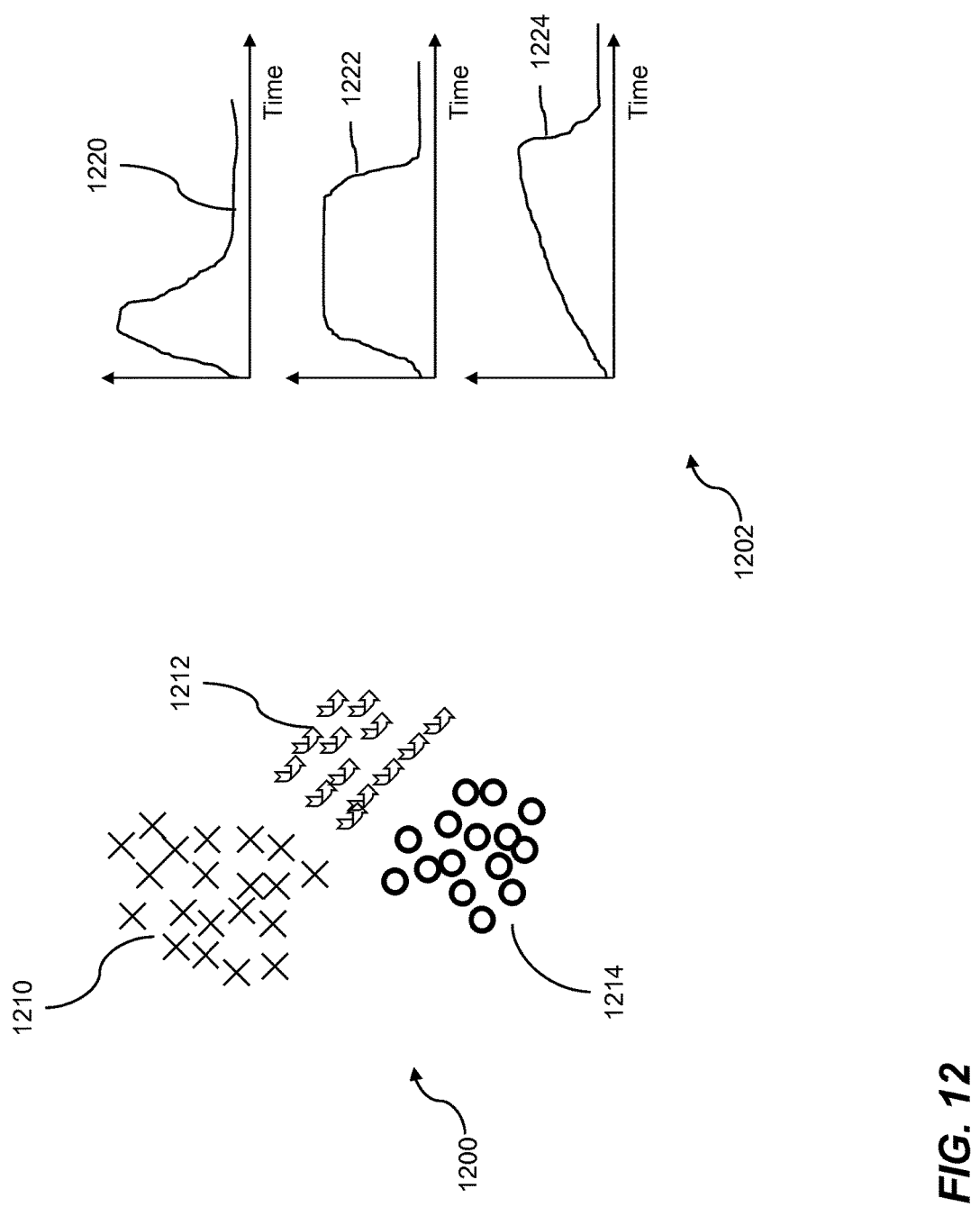
FIG. 12 shows example unsupervised clustering of features and characterizations of cluster profiles.

FIG. 12 shows example unsupervised clustering of features and characterization of cluster profiles. Features including samples of facial data can be clustered using unsupervised clustering. Various clusters can be formed, which include similar groupings of facial data observations. The example 1200 shows three clusters 1210, 1212, and 1214. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1202 can be generated based on the clusters that can be formed from unsupervised clustering, with time shown on the x-axis and intensity or frequency shown on the y-axis. The cluster profiles can be based on captured facial data including facial expressions, for example. The cluster profile 1220 can be based on the cluster 1210, the cluster profile 1222 can be based on the cluster 1212, and the cluster profile 1224 can be based on the cluster 1214. The cluster profiles 1220, 1222, and 1224 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 13A:
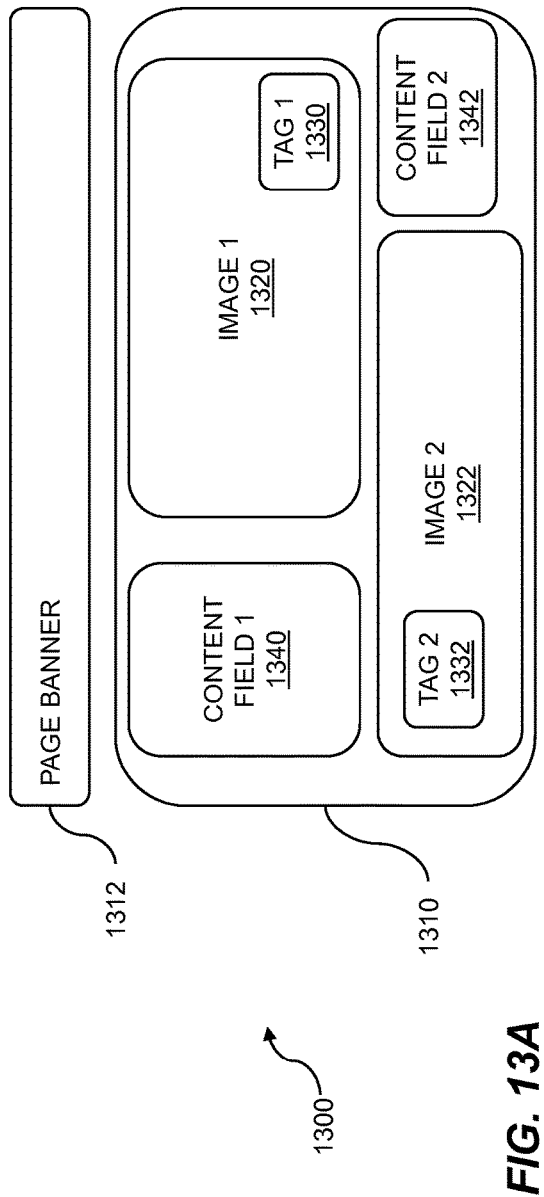
FIG. 13A shows example tags embedded in a webpage.

FIG. 13A shows example tags embedded in a webpage. Once a tag is detected, semiconductor based logic can be used to evaluate associated facial expressions. A webpage 1300 can include a page body 1310, a page banner 1312, and so on. The page body can include one or more objects, where the objects can include text, images, videos, audio, and so on. The example page body 1310 shown includes a first image, image 1 1320; a second image, image 2 1322; a first content field, content field 1 1340; and a second content field, content field 2 1342. In practice, the page body 1310 can contain any number of images and content fields, and can include one or more videos, one or more audio presentations, and so on. The page body can include embedded tags, such as tag 1 1330 and tag 2 1332. In the example shown, tag 1 1330 is embedded in image 1 1320, and tag 2 1332 is embedded in image 2 1322. In embodiments, any number of tags can be imbedded. Tags can also be imbedded in content fields, in videos, in audio presentations, etc. When a user mouses over a tag or clicks on an object associated with a tag, the tag can be invoked. For example, when the user mouses over tag 1 1330, tag 1 1330 can then be invoked. Invoking tag 1 1330 can include enabling a camera coupled to a user's device and capturing one or more images of the user as the user views a media presentation (or digital experience). In a similar manner, when the user mouses over tag 2 1332, tag 2 1332 can be invoked. Invoking tag 2 1332 can also include enabling the camera and capturing images of the user. In other embodiments, other actions are taken based on invocation of the one or more tags. For example, invoking an embedded tag can initiate an analysis technique, post to social media, award the user a coupon or another prize, initiate mental state analysis, perform emotion analysis, and so on.

Figure 13B:
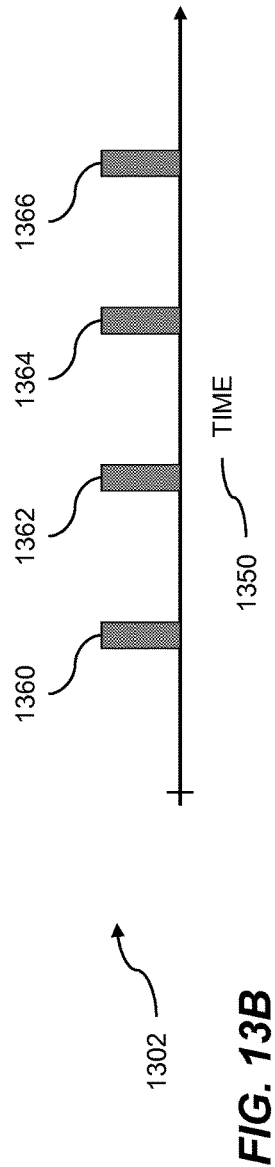
FIG. 13B shows example of invoking tags to collect images.

FIG. 13B shows example tag invoking to collect images. As stated above, a media presentation can be a video, a webpage, and so on. A video 1302 can include one or more embedded tags, such as a tag 1360, another tag 1362, a third tag 1364, a fourth tag 1366, and so on. In practice, any number of tags can be included in the media presentation. The one or more tags can be invoked during the media presentation. The collection of the invoked tags can occur over time, as represented by a timeline 1350. When a tag is encountered in the media presentation, the tag can be invoked. For example, when the tag 1360 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1360 does not enable the camera nor capture images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages and that enable the camera and image capture when invoked would be embedded in the media presentation. However, tags imbedded in the media presentation that are related to advertisements would not enable the camera when invoked. Various other situations of tag invocation are possible.

Figure 14:
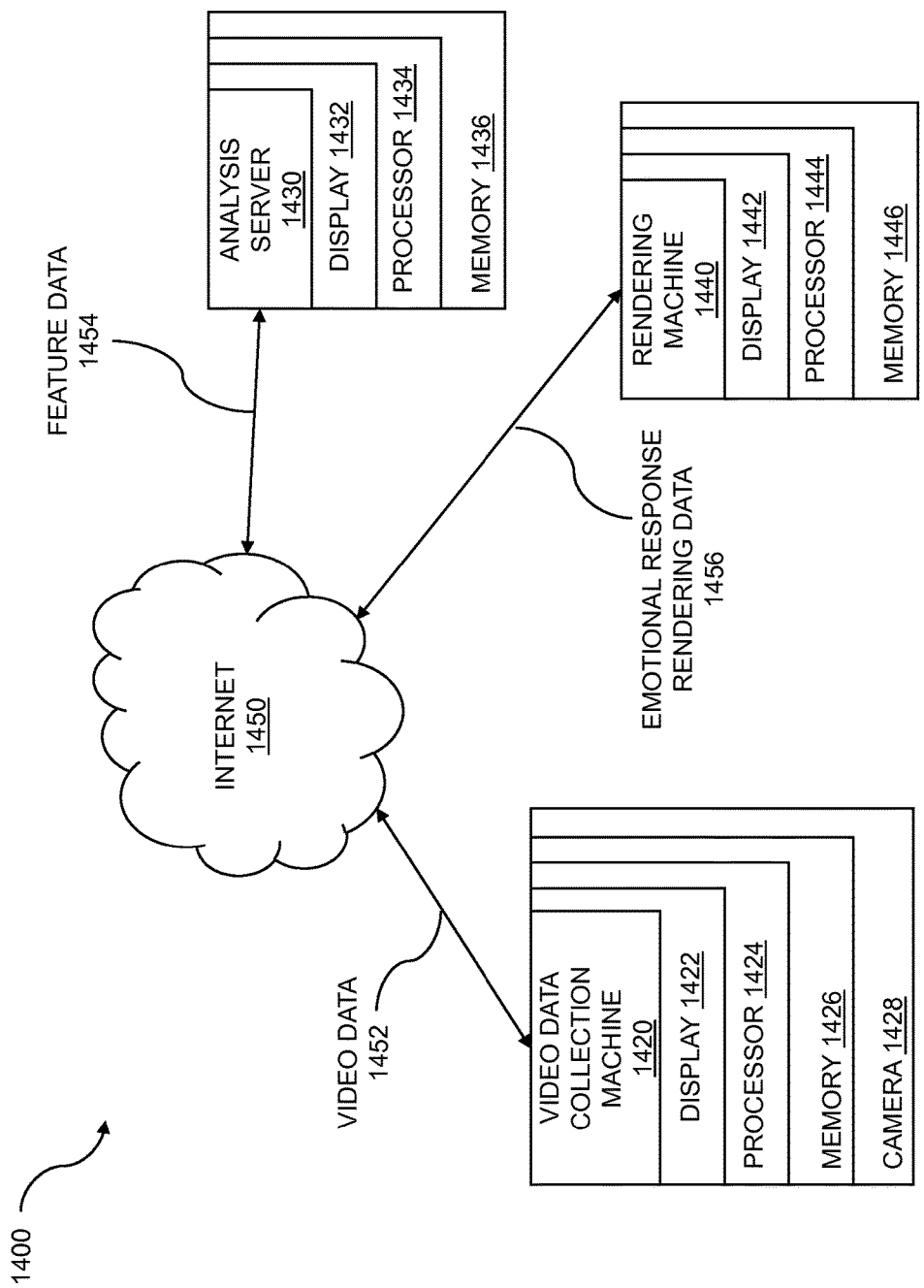
FIG. 14 is a system for mental state analysis.

FIG. 14 is a system for image and mental state analysis using an analysis device. The analysis device uses semiconductor based logic to perform or augment the needed analysis. An example system 1400 is shown for mental state data collection, analysis, and rendering. The system 1400 can include a memory which stores instructions and one or more processors attached to the memory, wherein the one or more processors, when executing the instructions which are stored, are configured to: obtain a plurality of videos of people; analyze the plurality of videos using classifiers; perform expression clustering based on the analyzing; and determine a temporal signature for an event based on the expression clustering. In embodiments, the semiconductor device sends images from the videos to a web service for external classification based on the emotion score. In some embodiments, the emotion score includes a facial expression and a probability of occurrence of the facial expression.

The system 1400 can provide an apparatus for analysis comprising: a device containing image analysis logic encoded in a semiconductor chip comprising: evaluation logic that evaluates bodies of one or more persons in videos; localization logic that performs localization of a face within the videos where the face is from one of the bodies of the one or more persons; feature extraction logic that performs extraction of regions of interest on the face; identification logic that provides identification of differences in the regions of interest within the face; classifier logic that employs image classifiers to map the regions within the face for emotional response content; and scoring logic that evaluates the emotional response content to produce an emotion score based on the face.

The system 1400 can provide a processor-implemented method for analysis comprising: using a device containing image analysis logic encoded in a semiconductor chip to perform: evaluating of bodies of one or more persons in videos; localizing of a face within the videos where the face is from one of the bodies of the one or more persons; feature extraction of regions of interest on the face; identifying of differences in the regions of interest within the face; mapping, using image classifiers, the regions within the face for emotional response content; and scoring the emotional response content to produce an emotion score based on the face.

The system 1400 can include one or more video data collection machines 1420 linked to an analysis server 1430 and a rendering machine 1440 via the Internet 1450 or another computer network. The network can be wired or wireless. Video data 1452 can be transferred to the analysis server 1430 through the Internet 1450, for example. The example video data collection machine 1420 shown comprises one or more processors 1424 coupled to a memory 1426 which can store and retrieve instructions, a display 1422, and a camera 1428. The camera 1428 can include a webcam, a video camera, a still camera, a thermal imager, a CCD device, a phone camera, a three-dimensional camera, a depth camera, a light field camera, multiple webcams used to show different views of a person, or any other type of image capture technique that can allow captured data to be used in an electronic system. The memory 1426 can be used for storing instructions, video data on a plurality of people, one or more classifiers, and so on. The display 1422 can be any electronic display, including but not limited to, a computer display, a laptop screen, a net-book screen, a tablet computer screen, a smartphone display, a mobile device display, a remote with a display, a television, a projector, or the like.

The analysis server 1430 can include one or more processors 1434 coupled to a memory 1436 which can store and retrieve instructions, and can also include a display 1432. The analysis server 1430 can receive the video data 1452 and analyze the video data using classifiers. The classifiers can be stored in the analysis server, loaded into the analysis server, provided by a user of the analysis server, and so on. The analysis server 1430 can use video data received from the video data collection machine 1420 to produce feature data 1454. In some embodiments, the analysis server 1430 receives video data from a plurality of video data collection machines, aggregates the video data, processes the video data or the aggregated video data, and so on.

The rendering machine 1440 can include one or more processors 1444 coupled to a memory 1446 which can store and retrieve instructions and data, and can also include a display 1442. The rendering of emotional response rendering data 1456 can occur on the rendering machine 1440 or on a different platform than the rendering machine 1440. In embodiments, the rendering of the event signature rendering data occurs on the video data collection machine 1420 or on the analysis server 1430. As shown in the system 1400, the rendering machine 1440 can receive emotional response rendering data 1456 via the Internet 1450 or another network from the video data collection machine 1420, from the analysis server 1430, or from both. The rendering can include a visual display or any other appropriate display format.

The system 1400 can include a computer program product embodied in a non-transitory computer readable medium for image analysis, the computer program product comprising: code for executing on a device containing image analysis logic encoded in a semiconductor chip where the code causes: evaluation logic to evaluate bodies of one or more persons in videos; localization logic to perform localization of a face within the videos where the face is from one of the bodies of the one or more persons; feature extraction logic to performs extraction of regions of interest on the face; identification logic to provide identification of differences in the regions of interest within the face; classifier logic to employs image classifiers to map the regions within the face for emotional response content; and scoring logic to evaluate the emotional response content to produce an emotion score based on the face.

Each of the above methods may be executed on one or more processors on one or more computer systems. Each of the above methods may be implemented on a semiconductor chip and programmed using special purpose logic, programmable logic, and so on. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"— may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. An apparatus for analysis comprising:
a device containing image analysis logic encoded in a semiconductor chip comprising:
evaluation logic that evaluates bodies of one or more persons in videos;
localization logic that performs localization of a face within the videos where the face is from one of the bodies of the one or more persons;
feature extraction logic that performs extraction of regions of interest on the face;
identification logic that provides identification of differences in the regions of interest within the face;
classifier logic that employs image classifiers to map the regions within the face for emotional response content;
scoring logic that evaluates the emotional response content to produce an emotion score based on the face, wherein the emotion score provides information on concentration based on the regions of the face including eyebrows where the eyebrows are furrowed; and
ranking logic that ranks an intensity of a plurality of facial expressions as a function of the emotion score.

2. The apparatus of claim 1 wherein the localization logic further performs localization of a second face within the videos.

3. The apparatus of claim 2 further comprising tracking logic for tracking the face and the second face.

4. The apparatus of claim 3 wherein the tracking logic provides an identifier for the face and the second face.

5. The apparatus of claim 4 wherein the tracking logic identifies that a face has left a video frame.

6. The apparatus of claim 5 wherein the tracking logic identifies that the face has returned to the video frame and associates information previously collected about the face from before the face left the video frame.

7. The apparatus of claim 1 wherein the identification logic further extracts one or more histogram-of-gradient (HoG) features from the regions of interest (RoI).

8. The apparatus of claim 7 wherein the scoring logic produces the emotion score based on the histogram-of-gradient features.

9. The apparatus in claim 1 wherein the extraction of regions is based on one or more of texture or shape.

10. The apparatus in claim 1 wherein the extraction of regions is based on motion within the face.

11. The apparatus in claim 1 wherein the identification of differences includes evaluation of eyebrow locations, eye locations, or mouth locations.

12. The apparatus in claim 1 wherein the classifiers are utilized by a support vector machine analysis to identify the emotional response content.

13. The apparatus of claim 1 wherein the classifier logic further identifies a gender, age, or ethnicity for the face.

14. The apparatus of claim 13 wherein the gender, age, or ethnicity is provided with an associated probability.

15. The apparatus in claim 1 wherein the identification of differences includes landmark detection within the face.

16. The apparatus in claim 1 further comprising storage memory coupled to the device.

17. The apparatus in claim 16 wherein the storage memory stores videos for analysis by the device to evaluate moods for people in the videos.

18. The apparatus in claim 16 wherein the storage memory stores classifier information used by the classifier logic.

19. The apparatus in claim 16 wherein the videos are retrieved from the storage memory for evaluation by the evaluation logic.

20. The apparatus in claim 1 wherein the emotion score includes a facial expression and a probability of occurrence of the facial expression.

21. The apparatus in claim 1 wherein the device further performs image correction for the videos including one or more of lighting correction, contrast correction, or noise filtering smoothing of the emotion score.

22. The apparatus in claim 1 wherein the emotion score is augmented by physiological information.

23. The apparatus in claim 1 wherein the emotion score is used to track a mood of a person with the face that is localized.

24. A computer program product embodied in a non-transitory computer readable medium for image analysis, the computer program product comprising:
   code for executing on a device containing image analysis logic encoded in a semiconductor chip where the code causes:
      evaluation logic to evaluate bodies of one or more persons in videos;
      localization logic to perform localization of a face within the videos where the face is from one of the bodies of the one or more persons;
      feature extraction logic to perform extraction of regions of interest on the face;
      identification logic to provide identification of differences in the regions of interest within the face;
      classifier logic to employ image classifiers to map the regions within the face for emotional response content;
      scoring logic to evaluate the emotional response content to produce an emotion score based on the face, wherein the emotion score provides information on concentration based on the regions of the face including eyebrows where the eyebrows are furrowed; and
      ranking logic to rank an intensity of a plurality of facial expressions as a function of the emotion score.

25. A processor-implemented method for analysis comprising:
   using a device containing image analysis logic encoded in a semiconductor chip to perform:
      evaluating of bodies of one or more persons in videos;
      localizing of a face within the videos where the face is from one of the bodies of the one or more persons;
      feature extraction of regions of interest on the face;
      identifying of differences in the regions of interest within the face;
      mapping, using image classifiers, the regions within the face for emotional response content;
      scoring the emotional response content to produce an emotion score based on the face, wherein the emotion score provides information on concentration based on the regions of the face including eyebrows where the eyebrows are furrowed; and
      ranking an intensity of a plurality of facial expressions as a function of the emotion score.

26. The apparatus of claim 1 wherein the scoring logic further determines an affect valence for a presentation based on the emotion score.

27. The apparatus of claim 26 wherein the affect valence describes an emotional reaction of an individual to the presentation.

28. The apparatus of claim 27 wherein the affect valence is positive or negative.

* * * * *